US011572513B2

(12) United States Patent
Ingolfsson et al.

(10) Patent No.: US 11,572,513 B2
(45) Date of Patent: Feb. 7, 2023

(54) INTEGRATED WASTE CONVERSION SYSTEM AND METHOD

(71) Applicant: YMIR TECHNOLOGIES EHF., Reykjavik (IS)

(72) Inventors: Oddur Ingolfsson, Kopavogur (IS); Asgeir Matthiasson, Reykjavik (IS); Sigurdur Ingolfsson, Kopavogur (IS)

(73) Assignee: YMIR TECHNOLOGIES EHF.

( * ) Notice: Subject to any disclaimer, the term of this patent is extended or adjusted under 35 U.S.C. 154(b) by 79 days.

(21) Appl. No.: 16/647,291

(22) PCT Filed: Sep. 17, 2018

(86) PCT No.: PCT/IS2018/050009
§ 371 (c)(1),
(2) Date: Mar. 13, 2020

(87) PCT Pub. No.: WO2019/053750
PCT Pub. Date: Mar. 21, 2019

(65) Prior Publication Data
US 2020/0216760 A1    Jul. 9, 2020

(30) Foreign Application Priority Data
Sep. 15, 2017 (IS) .............................. IS050189

(51) Int. Cl.
*C05F 17/00*     (2020.01)
*C11C 3/04*      (2006.01)
(Continued)

(52) U.S. Cl.
CPC ........... *C10G 3/00* (2013.01); *B01D 17/0205* (2013.01); *B01D 17/0217* (2013.01);
(Continued)

(58) Field of Classification Search
None
See application file for complete search history.

(56) References Cited

U.S. PATENT DOCUMENTS

| 4,263,744 A | * | 4/1981 | Stoller | A01G 18/40 47/1.1 |
| 5,536,856 A | * | 7/1996 | Harrison | B01J 8/226 261/114.5 |

(Continued)

FOREIGN PATENT DOCUMENTS

| CN | 102168109 A | 8/2011 | | |
| EP | 3050629 A1 | * 8/2016 | ........... | B01D 21/262 |

(Continued)

OTHER PUBLICATIONS

International Search Report and Written Opinion issued in PCT/IS2018/050009 dated Dec. 7, 2018.
(Continued)

*Primary Examiner* — Jennifer A Leung
(74) *Attorney, Agent, or Firm* — Heslin Rothenberg Farley & Mesiti, P.C.

(57) ABSTRACT

An entirely water-based, energy self-sufficient, integrated in-line waste management system is provided for comprehensive conversion of all organic fractions of municipal and wider community waste to fuels suitable for use in transportation, with all solid residues converted to high nutrition compost. The system is based on a combination of pre-treatment, involving alkaline hydrolysis and saponification; three-way separation of the pre-treated waste into different streams that are each directed to suitable further processing including fuel production; which includes biodiesel generation in a continuous-flow catalytic esterification unit, and anaerobic digestion to produce methane or other small
(Continued)

molecule biofuel. Remaining solids are converted to compost in a quasi-continuous process.

36 Claims, 14 Drawing Sheets

(51) Int. Cl.

| | | |
|---|---|---|
| C11C 3/10 | (2006.01) | |
| C12P 7/08 | (2006.01) | |
| C02F 11/04 | (2006.01) | |
| C10G 3/00 | (2006.01) | |
| B01D 53/62 | (2006.01) | |
| B01D 53/78 | (2006.01) | |
| B01D 17/02 | (2006.01) | |
| B04B 1/20 | (2006.01) | |
| B04B 1/04 | (2006.01) | |
| C12M 1/00 | (2006.01) | |
| B01J 3/04 | (2006.01) | |
| B01J 19/20 | (2006.01) | |
| B01J 3/02 | (2006.01) | |
| B01J 19/24 | (2006.01) | |
| C10G 1/00 | (2006.01) | |
| C05F 17/957 | (2020.01) | |
| C05F 17/40 | (2020.01) | |
| C05F 9/02 | (2006.01) | |
| C05F 1/02 | (2006.01) | |
| C05F 5/00 | (2006.01) | |
| C05F 7/00 | (2006.01) | |
| C05F 3/06 | (2006.01) | |
| B09B 3/45 | (2022.01) | |
| C05F 17/90 | (2020.01) | |
| D21C 1/02 | (2006.01) | |
| D21C 1/06 | (2006.01) | |

(52) U.S. Cl.
CPC ............ *B01D 53/62* (2013.01); *B01D 53/78* (2013.01); *B01J 3/02* (2013.01); *B01J 3/04* (2013.01); *B01J 19/20* (2013.01); *B01J 19/245* (2013.01); *B01J 19/249* (2013.01); *B04B 1/04* (2013.01); *B04B 1/20* (2013.01); *B09B 3/45* (2022.01); *C02F 11/04* (2013.01); *C05F 1/02* (2013.01); *C05F 3/06* (2013.01); *C05F 5/00* (2013.01); *C05F 5/002* (2013.01); *C05F 7/00* (2013.01); *C05F 9/02* (2013.01); *C05F 17/40* (2020.01); *C05F 17/90* (2020.01); *C05F 17/957* (2020.01); *C10G 1/002* (2013.01); *C11C 3/04* (2013.01); *C11C 3/10* (2013.01); *C12M 45/20* (2013.01); *C12P 7/08* (2013.01); B01D 2257/504 (2013.01); B01J 2219/0004 (2013.01); B01J 2219/00033 (2013.01); C10G 2300/1003 (2013.01); C10G 2300/4006 (2013.01); C10G 2300/4012 (2013.01); C10G 2400/04 (2013.01); C12P 2201/00 (2013.01); D21C 1/02 (2013.01); D21C 1/06 (2013.01); Y02E 50/10 (2013.01); Y02E 50/30 (2013.01)

(56) References Cited

U.S. PATENT DOCUMENTS

| | | | | |
|---|---|---|---|---|
| 2006/0293533 | A1* | 12/2006 | Iyer | C07C 67/03 |
| | | | | 554/174 |
| 2008/0050800 | A1* | 2/2008 | McKeeman | A23K 50/10 |
| | | | | 435/262.5 |
| 2009/0056201 | A1* | 3/2009 | Morgan | C12P 7/649 |
| | | | | 44/308 |
| 2010/0251608 | A1* | 10/2010 | Dumenil | C12P 19/02 |
| | | | | 435/167 |
| 2010/0313882 | A1* | 12/2010 | Dottori | C08H 8/00 |
| | | | | 127/37 |
| 2015/0064761 | A1 | 3/2015 | Lim et al. | |

FOREIGN PATENT DOCUMENTS

| | | | | |
|---|---|---|---|---|
| SK | 3702003 | A3 * | 2/2004 | ............ C05F 17/50 |
| WO | 2007033425 | A1 | 3/2007 | |

OTHER PUBLICATIONS

Debebe Yilma Dererie "Improved bio-energy yields via sequential ethanol fermentation and biogas digestion of steam exploded oat straw" Bioresource Technology, vol. 102, No. 6, Dec. 30, 2010, pp. 4449-4455.

* cited by examiner

INTEGRATED WASTE CONVERSION SYSTEM AND METHOD

CROSS REFERENCE TO RELATED APPLICATIONS

This application is a U.S. National Phase filing under 35 U.S.C. § 371 of International Application PCT/IS2018/050009, filed Sep. 17, 2018, and published as WO 2019/053750 A1 on Mar. 21, 2019. PCT/IS2018/050009 claims priority from Iceland application number 050189, filed Sep. 15, 2017. The entire contents of each of these prior applications are hereby incorporated herein by reference.

FIELD OF INVENTION

The invention is within the field of waste management and waste processing and specifically relates to processing of organic waste by suitable pre-treatment, separation and conversion of waste streams for producing valuable products including biodiesel and methane and/or ethanol.

INTRODUCTION

Waste management and treatment is a continuous challenge as the human population grows. Landfills use up land and have a limited lifespan before they fill up, creating a continuous demand, and when full, create land space with compromised usability and potential pollution problems. In the European Union, an adopted policy has set as target that by year 2020 landfilling should be limited to residual waste (i.e. non-recyclable and non-recoverable waste) (7th Environmental Action Programme (7th EAP)). Incineration solves problems of land-use, but create greenhouse gases, and high temperature incineration is required to prevent release of pollutants. It is well established in the literature, however, that incineration is incompatible with local environmental quality, efficient greenhouse gas reduction and the zero-waste targets of modern climate policy. Incinerators represent a prohibitively costly investment in many local contexts, their revenue model is weak, even assuming government energy subsidies and transportation of municipal solid waste (MSW) over long distances using fossil fuels. Incinerators are a major source of hazardous pollutants such as mercury, dioxins, and PCB. Importantly, their energy capture rate is notoriously low and the resulting energy only available for stationary uses. After incineration, some 15% of the original waste weight must still be committed to landfill as hazardous ash. Methane production/collection from landfills via anaerobic digestion is operated on small scale in many locations, but does not mitigate the general disadvantages of landfill use. Processes have been disclosed and implemented to produce fuel from waste, such as by intermediate syngas production that can be burned as fuel or converted to other fuels including gasoline or ethanol. Enerkem (Montreal, Canada) has built a fuel plant for making methanol (and eventually also ethanol) from waste, also through a syngas process. (See www.enerkem.com) The Enerkem process is an example of the well-known gasification process, where carbon-rich biomass is organic material is converted to carbon monoxide, hydrogen and carbon dioxide (this mixture being referred to as syngas) at a high temperature with controlled amount of oxygen. An alternative of the gasification process uses a plasma arc, where a high-voltage current is fed to a torch, creating a high-temperature arc. This is referred to as a plasma gasifier, InEnTec has built and demonstrated a small scale plant that can process 25 tons of waste per day using this technology (InEnTec, Richland, Wash., USA; www.inentec.com.)

Other, more flexible and less energy- and system demanding solutions would be appreciated.

BRIEF DESCRIPTION OF FIGURES

FIG. 4b shows a perspective exploded view of the main sections of the separation unit embodiment of 4a.

SUMMARY OF THE INVENTION

Figure 1A:
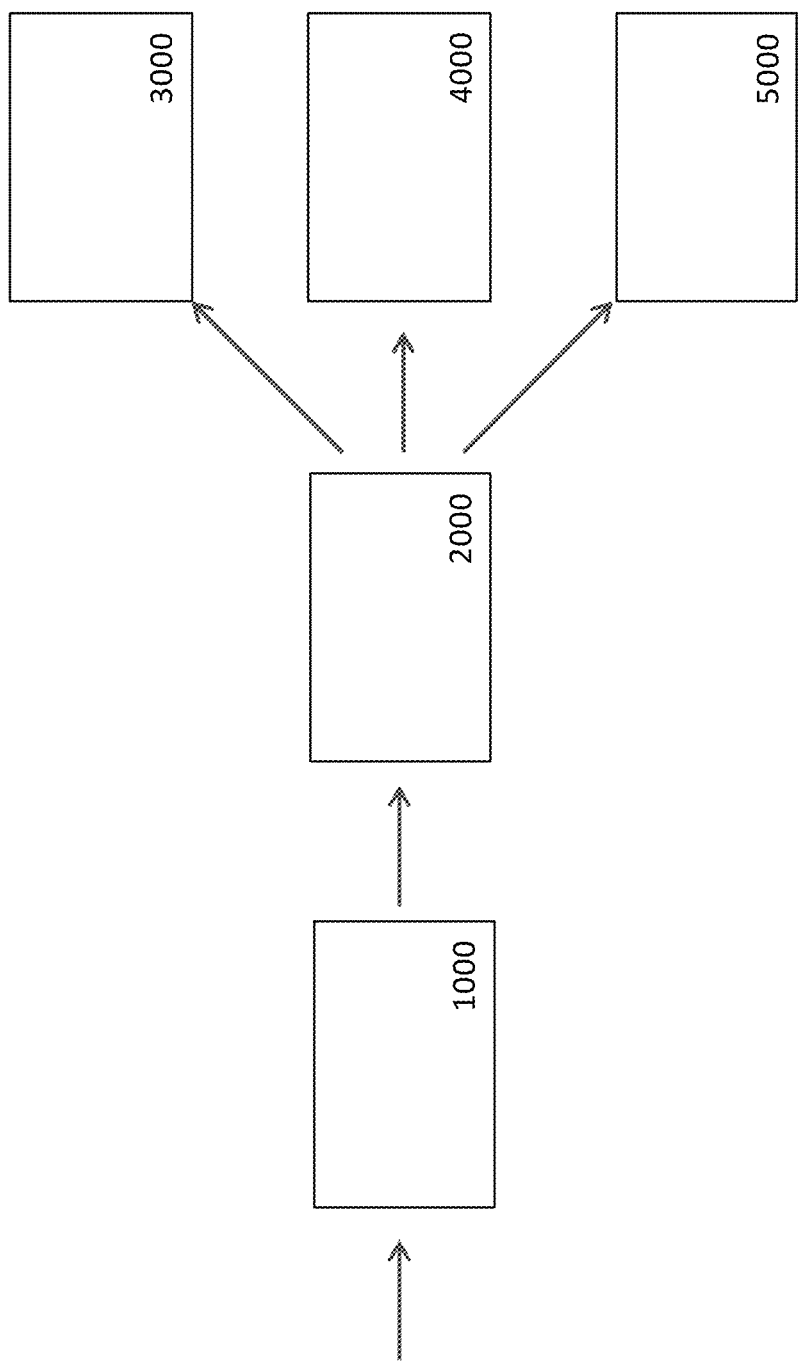
FIG. 1a shows a schematic depicting the main units of the system of the invention.

The present invention comprises an entirely water-based, energy self-sufficient, integrated in-line waste conversion system for comprehensive conversion of all organic fractions of municipal waste and wider community waste to fuels suitable for use in transportation, with solid residues converted to high nutrition compost. Entirely water-based refers here to the system processes not needing any organic solvents and no additives other than environmentally acceptable water-soluble chemicals. The system provides in short a complete treatment cycle for organic waste, minimizing or eliminating downstream waste expenditure and instead making valuable products. The system can be run entirely energy self-sufficient and offers flexibility, such that the system can accommodate very different waste streams, and does not require high temperature gasification, steam reforming or the like processes.

The system is essentially based on a flexible combination of pre-treatment, involving steam explosion hydrolysis and saponification; separation of the pre-treated waste into different streams that are each directed to suitable further processing including fuel production; fuel production which includes biodiesel generation in a continuous-flow catalytic esterification unit, and anaerobic digestion to produce methane or other small molecule biofuel such as ethanol (through fermentation). Remaining solids are converted to compost in a quasi-continuous accelerated composting process. Thus the system and process can advantageously be arranged so that may of the individual process steps are or can be operated in continuous mode, in particular, the pre-treatment including the steam explosion treatment, the three-phase separation, and the biodiesel production, whereas some other steps such as for example the accelerated composting can be operated in semi-continuous fashion. Collection and/or buffering tanks and containers can be arranged in between main units and process steps to accommodate transfer of material between different units and process steps, such as between continuous and semi-continuous phases and steps, and for any differences in output volume and input volume in adjacent units and steps.

It is particularly advantageous to operate the steam explosion treatment in continuous or semi-continuous fashion, this involves subjecting introduced material, preferably in alkaline or acidic solution, to high pressure and temperature, and discharging the material via sudden pressure-drop such as through a high-pressure rotary relief valve, with suitable arrangement as described herein below, such that the high-pressure and high-temperature retention section is maintained at a high operating pressure and temperature, while material is continuously or semi-continuously being introduced and discharged without pressure or temperature relief of the high-pressure and high-temperature retention section. This increases efficiency and reduces energy demands as compared to batch-operated steam explosion.

The system is suitably arranged in a modular fashion, allowing customization depending on the composition of waste to be processed at a given location. The system can be configured such that it is entirely or substantially water-based as defined herein, and most preferably all energy used in the process is generated from fuel components produced in the process.

The system is designed to maximize synergy between individual components beyond the current state of the art, to minimize energy consumption and carbon footprint and maximize environmental and economic benefit.

The system can readily be operated without any external energy input and energy balance calculations show that the system in general can be operated as a net contributor of energy, thus utilizing the energy content of the waste streams. Accordingly, in preferred embodiments, the system and process of the invention is energy self-sufficient, meaning that in such embodiments adding external energy is not required.

An aspect of the invention provides a waste conversion system, comprising at least one pre-treatment unit for receiving a stream of waste of which at least a portion thereof being organic waste, the pre-treatment unit comprising at least one continuous-flow steam explosion; at least one separation unit, for receiving a stream of pre-treated waste from the pre-treatment unit, the separation unit comprising at least one conditioning section and at least one separation section for the separation of conditioned waste into at least one fat/oil component, and at least one aqueous component and preferably as well at least one wet solid component; at least one biodiesel production unit, for generating biodiesel from the at least one fat/oil component; at least one digestion unit, for anaerobic digestion of the at least one aqueous component for the production of methane and/or a fermentation unit for the production of ethanol from the at least one aqueous component; and at least one composting unit, for the generation of compost from solid material.

Another aspect of the invention sets forth a process for treating and converting waste, comprising: receiving a stream of waste which comprises at least a portion that is organic waste; introducing the stream of waste or at least a portion thereof to a pre-treatment unit in which the stream of waste is introduced into a continuous-flow steam explosion reactor; directing a stream of pre-treated waste to a separation unit where it is separated into at least a component comprising fat and/or oil, and a component comprising aqueous slurry of organic matter, and preferably as well a component comprising solid organic material; introducing said fat and/or oil component into a biodiesel production unit, and generating biodiesel from said fat/oil component; introducing said component comprising aqueous slurry into a digestion unit and digesting said component through anaerobic digestion to produce methane or through fermentation to produce ethanol; and introducing remaining solid material into an accelerated composting unit.

Another aspect relates to a steam explosion reactor that comprises a high-pressure retention section and a pressure relief section and wherein said high-pressure retention section comprises at least one adjustable-speed conveyor for transporting said stream of waste through said section. The steam explosion reactor can further comprise at least one integrated carbon dioxide scrubbing unit that can optionally be configured to operate simultaneously with the steam explosion reactor.

Another aspect relates to a biodiesel reactor adapted to receive a continuous flow of at least one fat/oil component and thereby generate a continuous flow of biodiesel. The biodiesel reactor can be a continuous-flow biodiesel reactor that comprises a plurality of contact plates coated with esterification and/or transesterification catalyst for catalyzing esterification of free fatty acids and or transesterification of glycerides. The biodiesel reactor can further comprise one or more spacers and/or static mixers for adjusting the spacing between the contact plates and enhancing turbulent mixing.

Another aspect relates to a centrifugal decanter unit that comprises an axial bearing shaft, a decanter house coaxially enclosing a screw conveyor which is rotatable on said axial bearing shaft, at least one stationary centrally positioned main material inlet for feeding material into the screw conveyor, at least one solid matter outlet, a disc separator house enclosing said disc centrifuge, at least one impeller arranged between the decanter house and the disc separator house, and heavy phase and lighter phase outlets.

DESCRIPTION

Figure 1B:
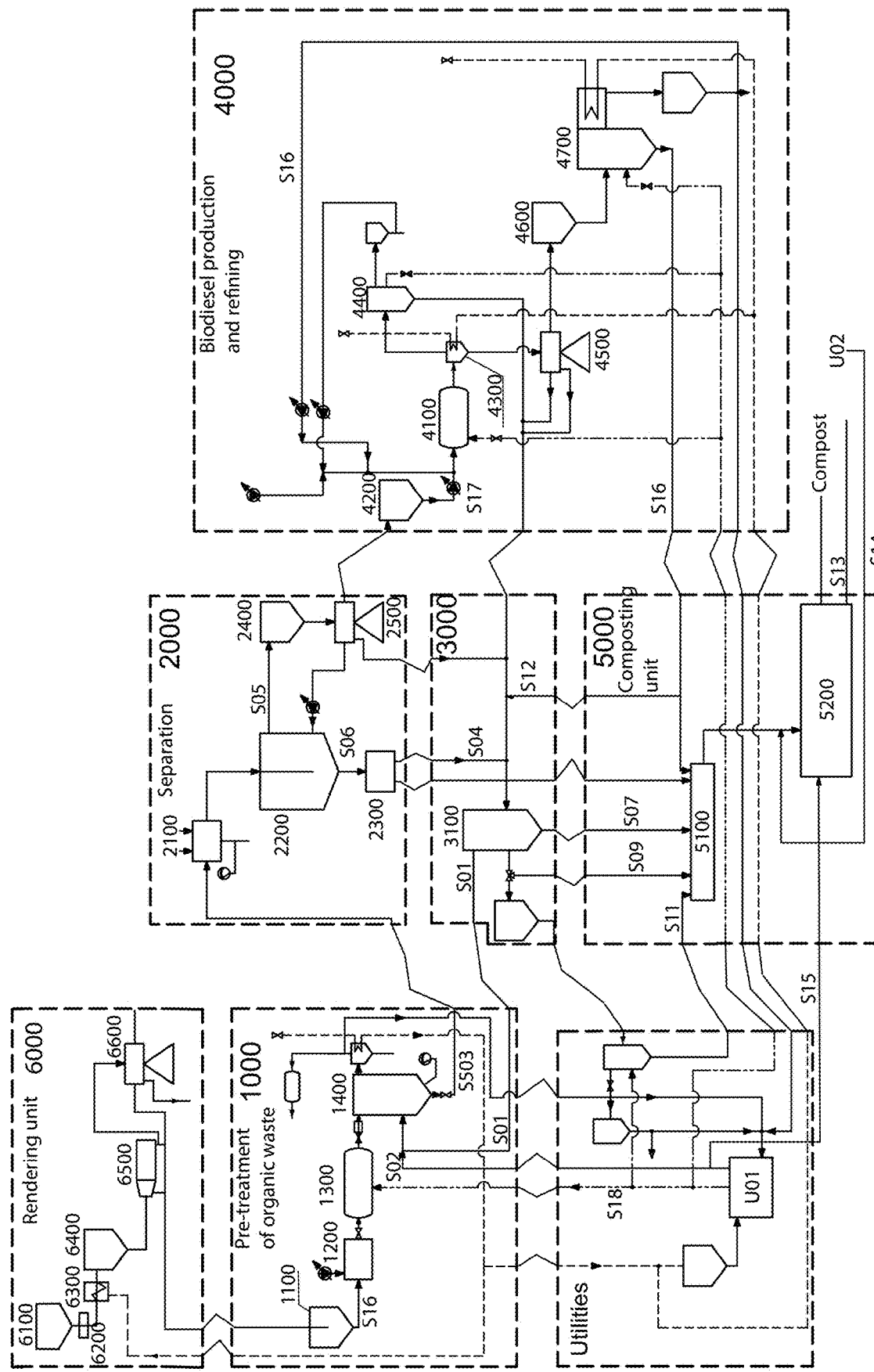
FIG. 1b shows a schematic diagram of an overall system of the invention.

The main units of the present invention are referred to in the schematic diagram in FIGS. 1a and 1b, which depict a pre-treatment unit (1000), a separation unit (2000), fuel production units (3000 and 4000) an accelerated composting unit (5000), and an optional rendering unit (6000). Each unit can have within it components and parts, the main parts of the system being referred to as sections. FIG. 1a shows a simplified schematic flow diagram of the units whereas FIG. 1b shows a more detailed schematic flow diagram overview of the system with sections and components of the units.

The term "water-based" indicates that no organic solvents are needed for the processes and system of the invention. In some embodiments, however, environmentally acceptable water-soluble reactants or chemicals may be applied, such as in particular ethanol or methanol necessary for biodiesel production and acids or bases to promote individual process steps, as further described below. The term "energy self-sufficient" indicates that the processes can be run without net adding of energy, and that all necessary energy, both thermal energy and electric energy can be provided by energy releasing steps in the process and/or by utilizing generated fuels as source of energy for the processes. In some embodiments the system may be hooked up to an external electrical grid for supplying to the system electrical energy but typically any such energy input to the system is more than counterbalanced by energy output of the system, meaning that the net energy production of the system is positive. The term oil/fat refers in general to any lipid from received waste including mono-, di-, and triglycerides derived from animal fat and oil and plant oil and free fatty acids from the same origin and any combination of these. The term biodiesel is used herein as is customary in the art and refers generally to fuel derived from recycled oil/fat material (and not petroleum based) that contains long-chain alkyl (methyl, ethyl and/or propyl) esters. The term compost has the meaning generally known in the art and refers to organic matter that has decomposed into fertilizer and soil amendment.

As mentioned, it is an advantage that the system of the invention can be configured entirely or substantially water-based. This means that all steps and sub-processes can be conducted without addition of an organic solvent, except for necessary (environmentally acceptable) water-miscible solvents that may be needed as reactant and are fully recovered from the respective conversion step, e.g. methanol or ethanol in the process steps for producing biodiesel.

The pre-treatment unit according to the invention receives the stream of waste, which is to be treated. The stream of waste can be of different composition, the system and process of the present invention is generally directed to organic waste, or waste comprising mostly organic matter, which may or may not be pre-sorted, such as but not limited to organic waste from general household waste. Accordingly, the waste material received for treatment can comprise but is not limited to one or more, or any combination, of the following: Household waste (HHW), slaughterhouse waste (SHW), food industry waste (FdIW), fish industry waste (FhIW), waste from the vegetable oil and the fish oil industry (OIW), sewage sludge, sewage grease and oils (SwW), agricultural waste such as wheat-straw or other straw, rice husk, soybean curd residue, and grass and animal manure (AcW), as well as garden waste (GW) and waste wood (WW). Such waste material streams may be categorized as carbohydrate (C), fat (F) and protein (P) rich streams or any combination of these. The terms fat, ("F"), "fat/oil", and "fat and/or oil" as used herein generally refer to components rich in lipids such as fat and/or oils including one or more of glycerides (mono-, di-, triglycerides), phospholipids and free fatty acids and any mixtures thereof.

If beneficial (depending on the waste material received), the system can further comprise an optional separator unit, upstream from the pre-treatment unit, for removing at least a portion of or preferably substantially all of at least one component of metals, glass, plastics and paper components and any mixes thereof from received mixed waste material. Preferably the incoming waste material to be treated is pre-sorted waste, such as from households, industry, and/or offices that sort waste such as into general plastic, metal, paper, and organic waste bins. From such sorted waste, the organic fraction can suitably be received and fully treated and converted in the system of the invention.

The pre-treatment unit comprises as its most basic components at least a continuous-flow steam explosion reactor, which in the presently preferred embodiments is operated as an alkaline steam explosion reactor as described in detail below. In these embodiments when operating the steam explosion process under alkaline conditions, the steam explosion reactor preferably comprises at least one integrated carbon dioxide scrubbing unit that receives the material discharged by pressure-relief from the high-pressure retention section of the steam explosion reactor. In one embodiment the continuous-flow alkaline steam explosion reactor comprises at least one high-pressure retention section, which is connected to the integrated carbon dioxide scrubbing section through a pressure relief connection through which a stream of material is delivered by rapid release of pressure from the high-pressure retention section into the carbon dioxide scrubbing section. The high-pressure retention section will generally be operated at a pressure in the range from about 10 bar (1.000 kPa) or from about 12 or from about 14 or from about 15 or from about 16, or from about 18 or from about 20 bar, to about 40 bar, or to about 38 bar, or to about 36 bar, or to about 34 bar, or to about 32 bar, such as to about 30 bar, such as to about 28, or to about 27 or to about 26 or to about 25 or to about 24 bar. In some embodiments the carbon dioxide scrubbing unit is operated at a pressure in a range from about 1 bar, such as from about 1.2 bar, such as from about 1.5 bar, such as from about 2 bar, to about 5 bar, or to about 4 bar, and alternatively provided with cooling elements for lowering the substrate temperature and for recapture of heat from the steam explosion unit.

The temperature in the high-pressure retention section is typically in the range of about 180-250° C., the selected temperature will typically depend on the desired pressure, meaning that the temperature and pressure are maintained in a relationship so that the pressure is around or just above the vapour pressure of water. For example, at a temperature of 180° C., the vapour saturation pressure of water is just over 10 bar, at 200° C. the saturation vapour pressure is about 15.5 bar, at 220° C. is about 23.2 bar, and at 250° C. the vapour saturation pressure is about 40 bar. In some embodiments the steam explosion reactor is operated at a temperature in the mentioned range and at a pressure corresponding to or close to the vapour saturation pressure of water at the respective temperature. Accordingly, in some embodiments, the steam explosion reactor is operated at a temperature in the range of about 180-200° C. and a pressure in the range of about 10-16 bar, in some embodiments the steam explosion reactor is operated at a temperature in the range of about 200-220° C. and a pressure in the range of about 15-23 bar, or in the range of about 220-240° C. and at pressure in the range of about 23-33 bar.

The steam explosion reactor effectuates abrupt disintegration of the unyielding structure of compact fiber materials making them accessible to efficient hydrolysis and subsequent decomposition through fermentation. The steam explosion unit further serves to effectuate hydrolysis and/or saponification of introduced organic waste material, such as celluloses, lignin, proteins and fats/oils, as well as extraction of soluble hydrocarbons, amino acids or peptides and fatty acids and salts thereof in the waste stream. When operating the steam explosion under alkaline conditions, the aqueous alkaline extract and the solid substrate are subsequently lowered in pH in the carbon dioxide scrubber described herein below. The pre-treatment process serves multiple purposes i) rupture of the structure of compact fiber material, ii) at least partial decomposition of low bio-availability material such as e.g., lignin and cellulosic material, iii) pre-hydrolysis of organic material, iv) aqueous extraction of nutrition from solid substrate and v) sterilization of all material.

The sterilization in the process is very advantageous as it widely enhances the utility for downstream products. Currently it is a challenge to effectively use certain waste streams from e.g. slaughterhouse facilities or fish or food processing plants, where waste can be contaminated with undesired bacteria, as well as household waste that often contains a significant amount of used diapers with urine and feces. The steam explosion treatment, in addition to the fragmenting and hydrolysis of material, provides desired sterilization. In many countries and regions use of food waste or other potentially bacterial waste such as for composting requires sterilization by autoclaving or the like. The present system provides such necessary sterilization of compost material, which accordingly is more acceptable and a higher value product.

As understood from herein, in preferred embodiments the carbon dioxide scrubbing unit constitutes an integral part of the continuous-flow steam explosion reactor when the steam explosion is operated under alkaline conditions. An upper part of the carbon dioxide scrubbing unit is preferably adapted to provide delivery of a stream of material from the high-pressure retention section of the steam explosion unit, such that flow of material through pressure relief directed to a cyclone-like pattern of the stream of waste within the carbon dioxide scrubbing section, but promoting splashing and dispersion towards the centre of the scrubbing section where the alkaline, aqueous waste material stream (the absorber) meets the carbon dioxide rich stream to be scrubbed, and thus enhances scrubbing efficiency. The term cyclone pattern as used herein refers to general circular or spiral pattern. The entrance angle of the waste stream and spiral-shaped guides inside the scrubber enhance the cyclone-like flow. The entrance angle is in some embodiments in the range of about 5° to 30° from horizontal, that is, downwardly tilted from horizontal, such as at angle in the range from about 5° or from about 10°, to about 30° or to about 25° or to about 20°. These are at the same time designed to partially disrupt the cyclone-like flow to cause effective splashing and dispersion of the incoming stream towards the centre region of the scrubbing section and maximize contact with the carbon dioxide rich gas stream. Thus, in some embodiments the scrubbing unit comprises at least one spiral-shaped insert and preferably at least two. In one embodiments the unit comprises two internal spirals vertically offset with respect to each other, with the upper spiral having clearance from the inner wall of the scrubber while the lower spiral has no clearance. This configuration serves to effectuate partial perpendicular velocity to the primary cyclone pattern flow of the stream of waste within the carbon scrubbing unit, effectuated by material conveyed from the upper spiral to the lower spiral along the inner wall of the carbon scrubbing unit. The lower spiral may further be provided with a corrugated pattern to partly guide material towards the centre of the scrubber unit, and preferably also having a protruding rim at its inner edge that causes the perpendicular component of the material to splash and disperse towards the centre.

Carbon dioxide flows into the carbon dioxide scrubbing unit through at least one carbon dioxide inlet which is preferably provided within a lower part of the carbon dioxide scrubbing unit, thus bubbles through the alkaline waste material accumulation at the bottom of the scrubbing section of the pre-treatment before rising through the scrubbing section and meeting the stream of dispersed alkaline material moving downwards within the scrubbing section. Optionally, the scrubber is equipped with heat exchanging cooling elements to lower the substrate temperature and to partially recapture the heat from the steam explosion. To maximize the heat exchange efficiency, such cooling elements may be installed in the condensation section at the bottom of the scrubber and/or in contact with the guiding spirals within the scrubbing unit. The cooling elements may advantageously be used to pre-heat water for a steam boiler of the system, further described herein.

The terms "carbon dioxide scrubber" and "carbon dioxide scrubbing" as used herein refer to that carbon dioxide is directed/injected into the scrubber to be adsorbed, thus the scrubber serves as regular carbon dioxide scrubber which has the general function of removing or reducing $CO_2$ content from a $CO_2$ rich stream; however, in the process the $CO_2$ is being utilized to lower pH and buffer the alkaline substrate/aqueous-extract (the absorber) generated in the pre-treatment process, and to increase carbonate and bicarbonate concentration of the extract for the purpose of enhancing anaerobic conversion of carbon dioxide to methane through methanogenesis in a subsequent methane conversion unit. As further described below, the system is advantageously operated by directing $CO_2$ that is generated in the system such as in the digestion unit and/or a boiler unit of the system into the carbon dioxide scrubber.

A secondary scrubber may be installed such that it is fed with the pre-filtered liquid fraction accumulating in the settlement region of the primary scrubber and may be in a conventional top-down spraying configuration, at elevated pressure and reduced temperature with the $CO_2$ lean exhorts from the primary scrubber fed from the bottom. Accordingly, a secondary scrubber in the system may in some embodiments be operated at a pressure in the range of about 5 to 150 bar, such as at a pressure value in the range from about 5 or from about 10 or from 15 or from about 20 or from about 30 or from about 40, to about 150 or to about 140 or to about 130 or to about 120 or to about 110 or to about 100 or to about 90 or to about 80 or to about 70 or to about 60 or to about 50 bar, and the temperature is preferably in the range 5 to 40° C. such as in a range from about 5° C. or from about 10° C. or from 1 about 5° C. or from about 20° C., to about 50° C. or to about 45° C. or to about 40° C. or to about 35° C. or to about 30° C.

Prior to introduction to the high-pressure steam explosion chamber, incoming material is preferably fed through a wetting and mixing section, where water can be added to the stream to obtain desired solid to liquid ratio and the material is mixed, and the pH can be affected, in particular for subsequent alkaline steam explosion, in which case alkaline solution is mixed into the stream in the wetting and mixing section. The wetting and mixing section preferably comprises a top-fed conveying mixer and wetting armature, such as one or more wetting nozzles. The exit port of the wetting and mixing section is preferably connected to the steam explosion reactor via a rotating-dosing valve and more preferably via a serial combination of a rotating-dosing valve and a high-pressure rotating valve, further described in detail herein below with reference to specific embodiments but applicable generally to the invention. The connection from the wetting and mixing section to the high-pressure retention section of the steam explosion reactor ensures that material can be continuously or semi-continuously transmitted from the ambient pressure wetting and mixing section to the high-pressure retention section, while the high-pressure is being continuously maintained in the latter.

In the high-pressure retention section, the loaded substrate is conveyed with suitable means from the loading point to the exit point such as but not limited to by means of an adjustable speed conveyor, preferably a screw conveyor. The section is equipped with at least one and preferably two or more steam injection ports and rotary valves at the loading and releasing end (referred to as feed valve and discharge valve, respectively) are preferably each equipped with steam injection port and pressure relief ports and are advantageously synchronized such that pressure drop in the high-pressure retention section is minimal during operation, and retention time in the high-pressure retention section is adjustable over a wide range, by adjustment of the conveying speed which is synchronized with the loading and relief mechanism of the feed and discharge valves. The synchronization is advantageously controlled via a control unit such as a PLC system.

The exit port of the high-pressure retention section is preferably connected vertically to a rotating dosing valve and a high-pressure rotary relief valve, as described further in the examples. At the exit time-point, the substrate is conveyed by the rotating dosing valve to a compartment of the high-pressure rotary relief valve, which at that time-point faces the exit port of the high-pressure retention section. The rotary valve then rotates to open the pressurized compartment to the pressure of the pressure relief section (the receiving section, which is preferably the carbon dioxide scrubber), enabling the steam explosion, before rotating to a re-pressurization position equipped with a steam injection port. From this position the compartment rotates back to the fill position.

There are however also within the scope of the invention other embodiments where instead of alkaline steam explosion acidic steam explosion is applied. These embodiments make use of essentially similar equipment arrangement, with some minor modifications, as there is no carbon dioxide scrubbing applied in these embodiments and instead of alkaline saponification the incoming waste stream is acidified with applicable acid solution such as with but not limited to hydrochloric acid partly resulting in the formation of free fatty acids from the fat/oil component, rather than saponification. After the acidic steam explosion and prior to the separation, pH of the steam explosion treated stream is raised by mixing with alkali as preferable.

The pre-treatment unit further comprises in some embodiments a grinding and/or homogenization unit that is arranged upstream of the continuous-flow steam explosion reactor. The grinding/homogenization unit can be of any suitable mechanical type, known to the skilled person, for grinding, and/or shredding or the like mechanical treatment of incoming material prior to further processing according to the invention.

The steam explosion reactor and in particular the alkaline steam explosion reactor with integrated carbon dioxide scrubber both in the general aspect disclosed herein and including all embodiments described and contemplated, is as such an essential aspect of the present invention, also independently from other units and components of other units within the system as a whole. Thus, the steam explosion reactor can be provided and used in other arrangements than those specifically disclosed and indicated herein as the complete system of the present invention.

When a waste stream is received that is rich in fat/oil, such as but not limited to slaughterhouse waste (SHW) or waste from the vegetable oil and the fish oil industry (OIW), such fat-rich stream can in certain embodiments be advantageously directed to a rendering unit, in which a pre-separation takes place, separating oily material from solid and aqueous material. The rendering unit is configured to separate from the incoming stream at least a portion of and preferably the bulk of a fat/oil component of the stream and reduce the volume of the remaining solids-containing aqueous slurry through water removal. This effects substantial volume reduction, and the remaining protein/carbohydrate-containing slurry fraction may be mixed with other organic waste and subjected to treatment (steam explosion) in the pre-treatment unit. The fat/oil component that is obtained from the rendering unit can however be subjected directly to the biodiesel unit further described below and the aqueous component may be sufficiently freed of organic components to be directed to sewage or applicable waste treatment. The rendering unit is applicable and useful for waste streams, which can be readily separated into their respective water-, oil/fat and protein components (after grinding where advantageous). The rendering typically involves a period of moderate heating at atmospheric pressure (typically within a range of about 80-100° C. such as more preferably in a range of about 90-95° C., for a period of time such as in the range of about 30-60 min) followed by centrifugal separation. Accordingly, the rendering unit comprises in some embodiments a heating/retention tank, a decanter and centrifuge, or a combined unit comprising the functionality of the decanter and the centrifuge as described herein in a special embodiment of the three-phase separation unit. Remaining solids-containing fraction from the rendering unit is then advantageously directed to the pre-treatment unit, for sterilization and hydrolysis as described above. This increases the efficiency of the system as the load on the pre-treatment unit can be substantially reduced.

The separation unit of the system according to the invention comprises in some embodiments a conditioning section, a continuous fat/oil separation section, a liquid/solid separator, and a centrifugal purifier. In some embodiments the conditioning section of the separation unit comprises a chamber with a mixer and means (such as armature) for introducing acid solution (and/or other solution) such as for pH adjustment of pre-treated waste material contained in the chamber, and further a discharge valve for discharging conditioned material. The mixer within the conditioning unit may be any of a selection of suitable mixers known to the skilled person, in some embodiments the mixer is a conveying mixer. The continuous fat/oil separation section comprises in preferred embodiments a vertically arranged elongated tank within which is located an elongated tube centrally and coaxially. A discharge valve is preferably arranged at the entry of said central tube, by which conditioned material can be discharged from the conditioning section of the unit into the tube. The tube or tank preferably comprises one or more micro-bubble injector(s) near the lower end of the tube, and an exit valve. The fat/oil separation section further preferably comprises means for feeding fat/lipid accumulating on the liquid surface within the tank to a fat/oil buffer tank or the centrifugal purifier, such as but not limited to surface pump and/or overflow drain pocket. The liquid/solid separator is in some embodiments configured as a conveyor (e.g. screw conveyor) enclosed in a housing, such as a screw conveyor in a cylindrical housing, which is arranged at an angle; the aqueous slurry from which fats and oils have been separated is fed into the screw conveyor at an entry by the lower end of the cylindrical housing, the screw conveyor conveys solids material upwardly through the housing towards an exit port for a fraction comprising solids, the exit port being at or near the upper end of the housing/conveyor. The conveyor and housing may be arranged at an angle in a range of about 5-45°, such as at an angle in the range from about 5° or from about 7° or from 10° or from about 12°, to about 45° or to about 40° or to about 35° or to about 30° or to about 25°.

When alkaline steam explosion is being applied, with an integrated carbon dioxide scrubber, the slurry exiting the carbon dioxide scrubber enters the condition section and is typically further pH adjusted (the pH having been lowered in the scrubber by means of the CO2). Where a secondary scrubber is installed the effluent from the secondary scrubber is combined with the slurry from the primary scrubber prior to this pH adjustment. The pH adjustment effectuates that alkaline salts of fatty acids are converted to free fatty acids and can thus be separated from the aqueous phase through flotation. This takes place in the continuous fat/oil separation section. Thus, the three-phase separation section provides (i) a fraction comprising free fatty acids along with remaining non-hydrolyzed fats and oils; (ii) a fraction comprising the aqueous extract, preferably with less than 15% suspended solids and more preferably less than 12% or less than 10% suspended solids and yet more preferably less than 8% or less than 6% solids, this being adjustable; and (iii) a fraction comprising a solid substrate, which generally refers to a fraction having preferably at least 25% dry material content and more preferably higher dry material content such as at least 28% or at least 30%, and yet more preferably at least 35% or at least 40%, and more preferably at least 45% or at least 50%, such as at least 55% or at least 60%. The dry material content of the solid substrate and the suspended solid fraction in the aqueous phase is adjustable, such as by adjustment of the extent and perforation density and the hole size of the perforated bottom plate of the solid/liquid separation section as further described below.

The first-mentioned fat/oil fraction can advantageously be directed to the biodiesel unit to be subjected to esterification and/or trans-esterification. As mentioned, the biodiesel unit is advantageously adapted to receive a continuous-flow of a fat/oil component from the separation unit and to function as a continuous-flow biodiesel production unit. This means a unit producing essentially a continuous-flow of biodiesel.

In a preferred embodiment according to the invention the separation section comprises a centrifugal decanter unit combining all sections of a three-phase separation unit in one and the same instrument. Such unit generally comprises a combined screw conveyor decanter and a disc centrifuge, which is also referred to as a conical plate centrifuge, a disc bowl centrifuge, and a disc stack separator, these terms being synonymous in the context herein. These functional components form a decanter section and centrifuge section, respectively. The centrifugal decanter generally comprises a decanter house that encloses a screw conveyor, the decanter house and conveyor are independently rotatable on an axial bearing shaft. The decanter section further comprises at least one inlet which is preferably arranged stationary and axially, inside an axial bearing shaft. The inlet feeds material into the decanter house. A solid matter outlet is arranged in proximity to the distal end of the screw conveyor (the end away from the centrifuge section). The unit further comprises a disc separator house enclosing the mentioned disc centrifuge. At least one impeller is arranged between the decanter house and the disc separator house that transmits liquid there through, a heavy phase outlet and a lighter phase outlet, the impeller is preferably stationary. The centrifugal decanter unit described herein and in further detail in the examples can as such function independently, for desired separation of organic streams with water, oils and solid matter and can in certain aspects be provided as an independent unit, suitable for a system as disclosed herein but also in different systems and applications.

In accordance to the invention, the biodiesel production unit comprises in a preferred embodiment a modular continuous-flow biodiesel reactor that comprises contact plates coated with esterification catalyst for catalysing esterification of free fatty acids and/or for trans-esterification of glycerides. The term "contact plates" indicates that the plates come in contact with the introduced fat/lipid material. The plates are in some embodiments corrugated, to increase surface area and improve flow dynamics and contact. Preferably one or both sides of the contact plates are coated with immobilized catalytic material depending on the flow configuration. Esterification catalysts are as such known in the art, and a suitable catalyst can be selected by the skilled person. The catalyst is in some embodiments a solid-state catalyst or can in other embodiments be an enzyme catalyst, which may or may not be immobilized on a solid substrate. The reactor may further comprise spacers for adjustable separation of the contact plates, the spacers may as well be coated with catalyst, and preferably the spacers have flow perturbing inner surface, to enhance turbulent flow and efficient mixing. Preferably a mixer is arranged within the reactor between contact plates, such as but not limited to one or more static mixers. Preferably a plurality of static mixers are arranged in between contact plates, these can be but are not limited to vertically extending profile members, such as V-shaped profiles, curved profiles, bars, meshes or the like.

In some embodiments contact plates in the reactor are arranged with catalyst on one side and the plates being arranged such the coated sides face each other, and material flow being directed through the reactor such that reactant media flows between the catalyst-coated sides and thermal media flows in the channels between non-coated sides.

In some embodiments at least one homogeneous catalyst is applied, which can be but is not limited to an acidic catalyst, such a sulphuric acid, or an alkali catalyst such as but not limited to sodium hydroxide, sodium methoxide or potassium hydroxide or potassium methoxide. Conventional homogeneous alkaline catalyst however is not applicable to raw materials comprising a substantial amount of free fatty acids. Accordingly, in some embodiments at least one heterogeneous catalyst is applied, which can be an organic or inorganic catalyst, such as are known in the art or enzymatic catalyst. In some embodiments such as further described below, a combination of catalysts is used in separate reactors or separate reactor sections, wherein a first catalyst catalyses esterification of free fatty acids and a second catalyst catalyses transesterification of glycerides in a second section. Where combination of catalysts is used in separate reactors, intermediate purification through flash evaporation or resins may be introduced between the reactors. Intermediate resin purification may also be introduced where a single catalyst or combination of catalysts is used in a single reactor arrangement.

The reactor is preferably equipped with an inlet system to allow for effective mixing of the reactants prior to injection into the reactor, which includes the addition of an alcohol (methanol/ethanol) as needed in the production reaction. In some embodiments ethanol produced within the system is used as reactant in the biodiesel production. In some embodiments additional homogeneous catalyst can be added through the inlet. Such additional catalyst can be a liquid catalyst, added as additional catalyst and/or for activation of solid-state catalyst on the plates in the reactor. The inlet system can comprise a pre-mixer, to mix conditioned reactant material with a co-solvent and/or to mix additional catalyst such as sulphuric acid with co-solvent. A useful co-solvent comprises methyl esters and may preferably be provided through partial circulation of the produced biodiesel. The pre-mixer can be double-stage, meaning that at a first stage certain materials are mixed, and at a second stage those materials are mixed with other substance or substances that may or may not be pre-mixed at an additional pre-mixer. In the reactors, the plates are preferably stacked with alternating two coated surfaces facing each other and two non-coated surfaces facing each other. Any other sequence of stacking is optional if advantageous.

In some embodiments the continuous-flow biodiesel reactor is encapsulated in an outer enclosure, in particular when high-pressure operation is desired, the enclosure may for example be a differential pressure equalizer comprising a sealed casing. The inlet and exit ports of the reactor (for reactants and/or thermal fluids) can in some embodiments extend outside the casing though high-pressure tubular sealing.

In some embodiments the reactor is divided in sections where it is advantageous to run esterification of FFAs and transesterification of the glyceride fraction separately. In such configurations one or both sections may be run with homogeneous catalysts with adequate purification/conditioning as an intermediate step. Accordingly, in some embodiments the biodiesel comprises at least two serially connected reactors or reactor sections. In one such embodiment esterification with homogeneous acid catalyst is effectuated in the first reactor/reactor section and transesterification with homogeneous basic catalyst is effectuated in the second. Where such separation is applied between the esterification and transesterification, purification and water removal may be effectuated through flash evaporation and ion exchange between said esterification and transesterification reactors or sections.

To generate the catalytic surface where a solid state catalyst is preferable, the surfaces confining the reaction channel of the continuous-flow biodiesel reactor may be coated in one or more steps, by e.g., precipitation and calcination, thermal spray coating, chemical vapour deposition, reactive coating, atomic layer deposition or any other coating method or combination of these, providing a rough, high surface-area coating protruding from the surface.

Where applicable, metal sponges (e.g., titanium or zirconium) or porous structures may be directly grown on the surface or brought on to the surface from powders of the respective metal sponges.

Doping, where advantageous, may be achieved in the same step or through e.g. chemical vapour deposition. Controlled oxidation may then proceed thermally assisted, or non-thermally-assisted, through exposure to the appropriate oxidizing media in gaseous or liquid form, e.g., air, oxygen, oxidative solutions of metal salts or oxides. Direct coting with oxides may also be achieved through direct precipitation on the native or pre-treated surface and consecutive calcination.

The coating provides at the same time for the desired catalytic activity and efficient microscopic mixing at the high share surface.

Where enzymatic catalysis is applied, immobilization is preferably achieved through covalent bonding to an inorganic substrate with large surface areas such as silica or aluminium oxide, but may also be achieved through physisorption or encapsulation and where advantageous the substrate may be organic material such as e.g., starch or collagen.

The biodiesel reactor as described herein and all embodiments thereof including but not limited to the embodiments exemplified in further detail in the examples can as such function independently for any biodiesel production and is such not limited to operation in a waste conversion system as disclosed herein but also in any generic biodiesel production.

The aqueous extract fraction from the three-phase separation unit is preferably subjected directly to thermophile anaerobic digestion for methane production and/or to fermentation for the production of ethyl alcohol in the digestion unit of the system, as further described in detail below. Both processes as such are well known in the art. Generally, ethanol production by fermentation will include adding or maintaining active yeast in the fermentation tank into which the aqueous carbohydrate-rich stream is fed. In some embodiments of the invention, a single unit is configured so that it can either produce methane or ethanol, and the user can switch between the two production modes depending on the incoming waste streams. This is in short achieved by cleaning out the unit and in the case of initiating methane production, a stock comprising feed bacteria is introduced, whereas in the case of ethanol production a stock comprising yeast is introduced. In other embodiments, two units can be arranged so that one is dedicated to methane production and the other to ethanol production by fermentation.

The fraction comprising the solid substrate from the three-phase separation unit is directed to the accelerated composting unit of the system. The accelerated composting unit is preferably a three-stage semi-continuous unit. In such three-stage semi-continuous unit according to the invention the first stage serves for mixing and initiation, where fresh substrate is mixed with seed compost. The substrate, emerging from the three-phase separation unit is preferably at a temperature in the range of about 40-50° C. at this stage, and may thus be subjected directly to thermophile composting, bypassing the mesophilic stage. Further, through the rupture of the structure of dense cellulosic or lignin rich material, the pre-hydrolysis of cellulosic and lignin material and decomposition of the protein component to shorter peptides and amino acids in the steam explosion pre-treatment unit, the thermophile digestion is considerably accelerated and the high digestibility of C rich material allows for comparably low C:N ratio in the initiation phase. This phase is preferably maintained under continuous or semi-continuous mixing preferably for a period in the range from about 2 to about 6 hours, and more preferably within a range from about 3 to about 6 hours, such as a range of about 3-5 hours or a range of about 4-6 hours, such as about 3 hours, about 4 hours, about 5 hours or about 6 hours, before transfer to stage two.

As the organic material transferred to the composting unit has been subjected to steam explosion treatment, providing sterilization of potential pathogenic material and increased digestibility of carbon-rich cellulose material, paper, diapers etc. the composting process in the invention can accommodate a wider carbon:nitrogen ratio (C:N) than in conventional composting. In some embodiments, however, the C:N is monitored or assessed based on the incoming waste stream, and the C:N ratio of the composting material adjusted with carbon-rich material such as but not limited to garden waste, glycerol (e.g. from the biodiesel production of the system) flour, dough, fruit and other carbon rich disposal from the food industry and high sugar content solid disposal from other sources. The C:N ratio in the initiation step is balanced to achieve a ratio preferably in the range from about 10 to about 20, and preferably in the range from about 15 to about 20, but may also be driven with C:N in the range from about 10 to about 15.

In the stage one mixing and initiation step, in some embodiments a fraction of sludge removed from the anaerobic digestion and or fermentation can advantageously be mixed into the compost substrate.

After the first step, the compost substrate should preferably be at or close to the peak of its thermophile stage and is then transferred to a second stage and is transferred to the second stage under admixing of bulking materials such as wood chips, preferably such reclaimed after the third, aging step of previous batch but may also or alternatively be of other origin such as from garden waste. The bulking material is preferably continuously mixed with the substrate in the transfer of substrate from the first (initiation) stage to the second (incubation) stage, such as in a conical screw conveyer, preferably configured such that its volume increases appropriately along the transfer direction. Thus in some embodiments substrate is transported from the initiation section to the incubation section with a conveyor such as a screw conveyor, where the conveyor increases in volume/diameter at a section along the conveying direction, such as via a conical screw conveyor, preferably such that the diameter or volume increases by a factor in the range of about 20-50%. A suitable feeder, such as hopper, may be arranged and joined to the widening section of the conveyor, for feeding the bulking material thereto. The second stage, the incubation stage, is in some embodiments without agitation, but is preferably with active (forced) aeration and humidification. In this second stage the thermophile phase is completed or almost completed, preferably in a period in the range from about 24 to about 96 hours, after which the substrate is transferred to the third stage, referred to as the aging stage. In the third stage, the substrate is subjected to maturing as appropriate, typically for the duration in the range from about three months to about one year, such as in open-air piles or other suitable and fitting arrangements.

DETAILED DESCRIPTION

In the following, exemplary embodiments of the invention will be described, referring to the figures. These examples are provided to provide further understanding of the invention, without limiting its scope.

In the following description, a series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

Figure 2:
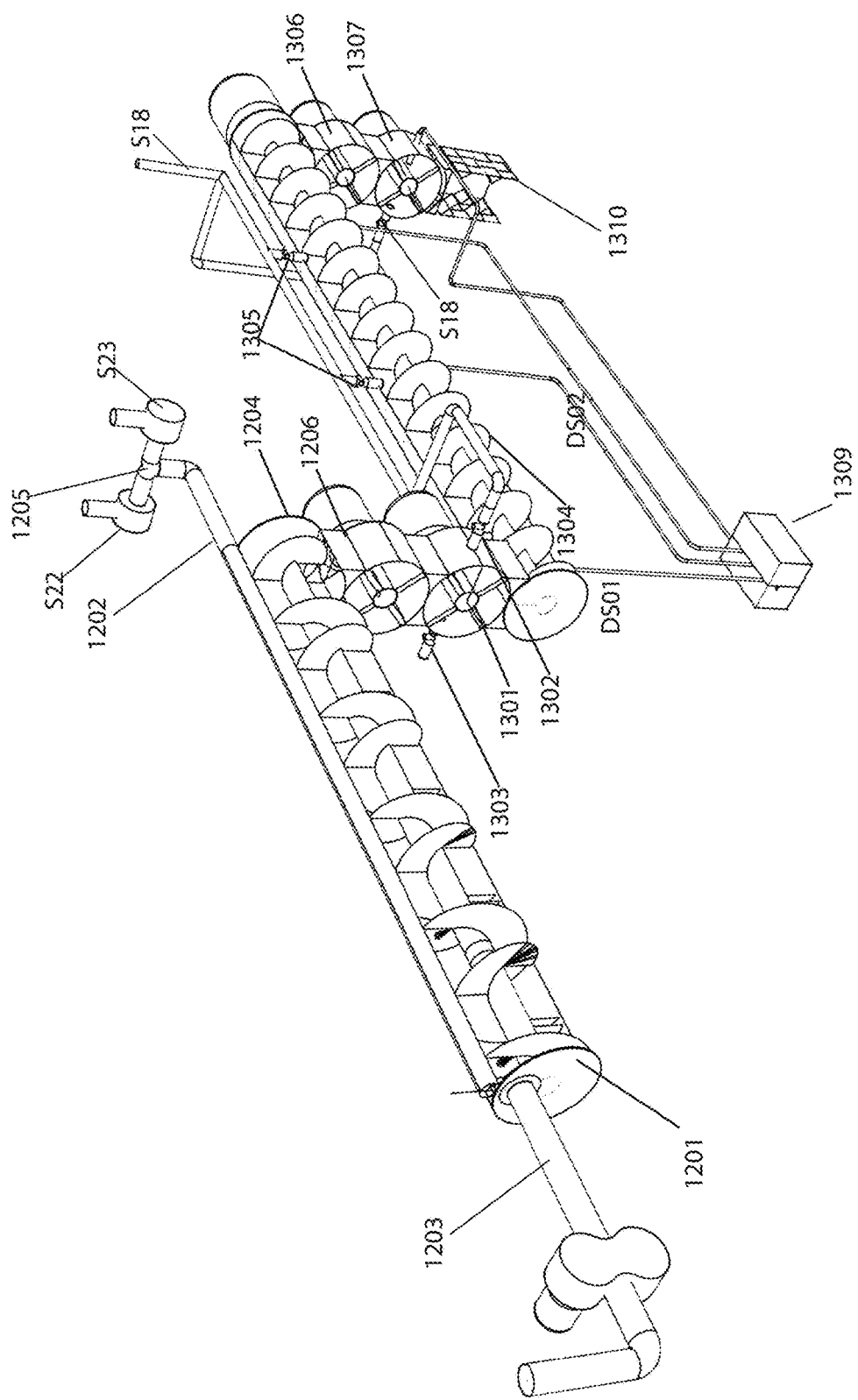
FIG. 2 shows an explosive perspective illustration of a portion of the pre-treatment unit, specifically the wetting and mixing section and the high-pressure heating and retention section.
Figure 6A:
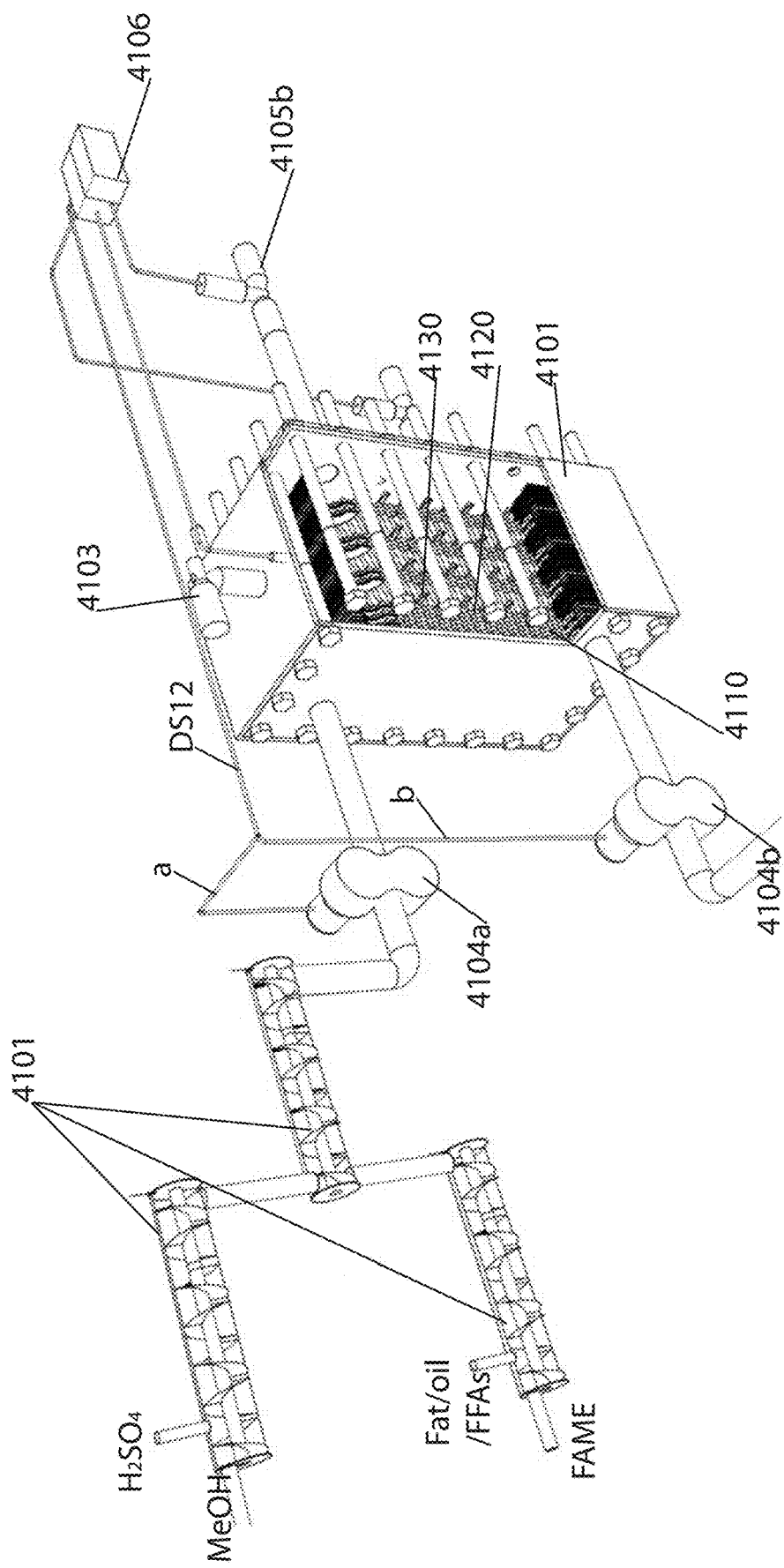
FIG. 6a shows a perspective overview of a continuous-flow biodiesel reactor of the invention.
Figure 6B:
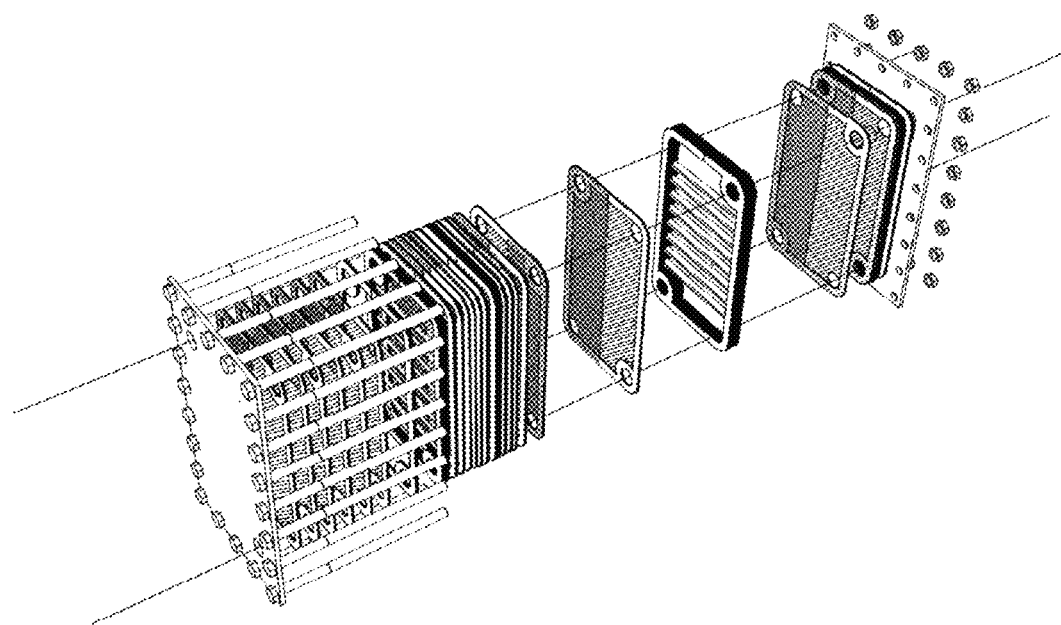
FIG. 6b shows further details of the continuous-flow biodiesel reactor from FIG. 6a, illustrating possible stacking of the reactors components and material flow in the conversion process.
Figure 6C:
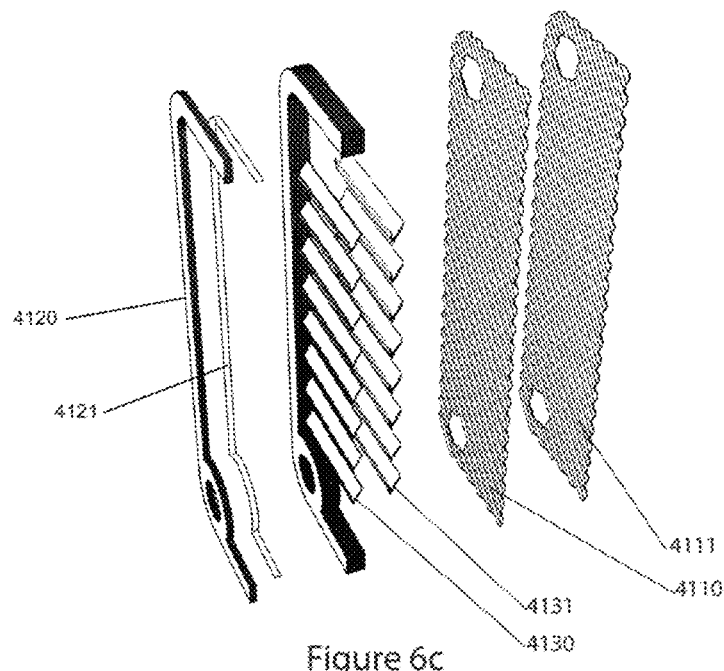
FIG. 6c shows a perspective view and cross-section of a cell unit within the continuous-flow biodiesel reactor, on the right a corrugated contact plate 4110, with 4111 showing the surface coating in an expanded cross-section; in the centre is a static mixer 4130, with flow-perturbing surface coating 4131 shown in expanded cross-section; and on the left a spacer 4120 with catalytic surface coating 4121 shown in expanded cross-section.
Figure 6D:
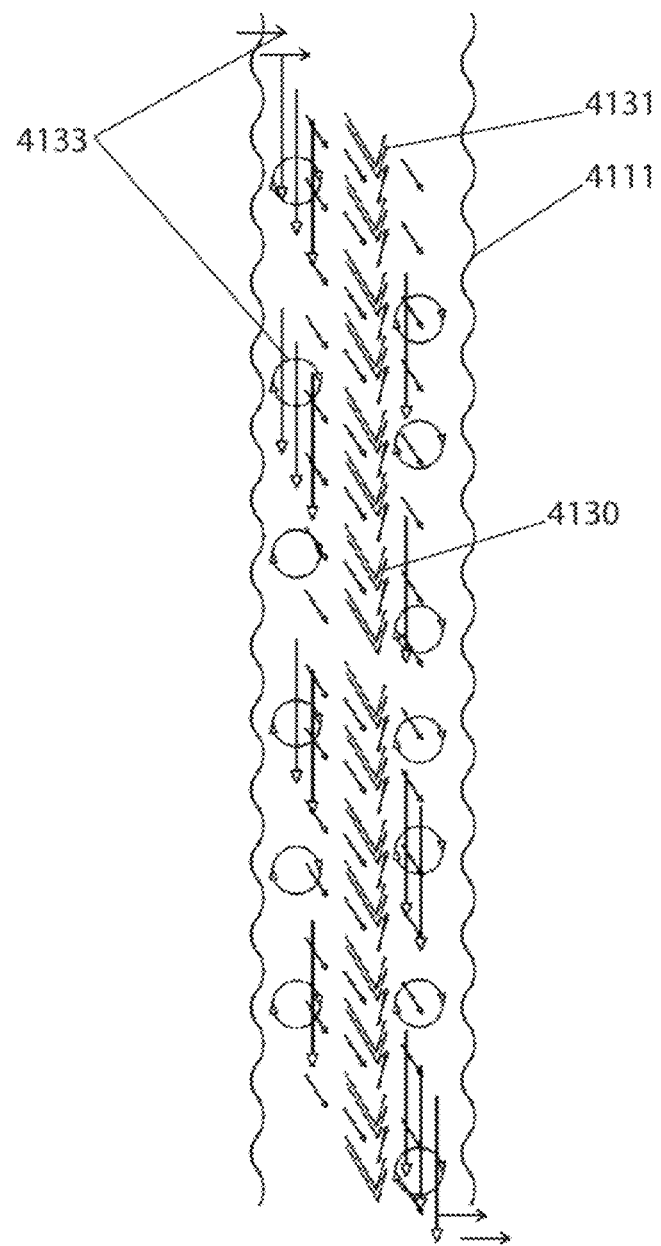
FIG. 6d shows an expanded cross-section example of flow lines within one cell of the continuous-flow biodiesel reactor composed of a static mixer confined by two reactor plates. All surfaces are shown coated with catalytic material. The cell is shown without spacers.
Figure 7A:
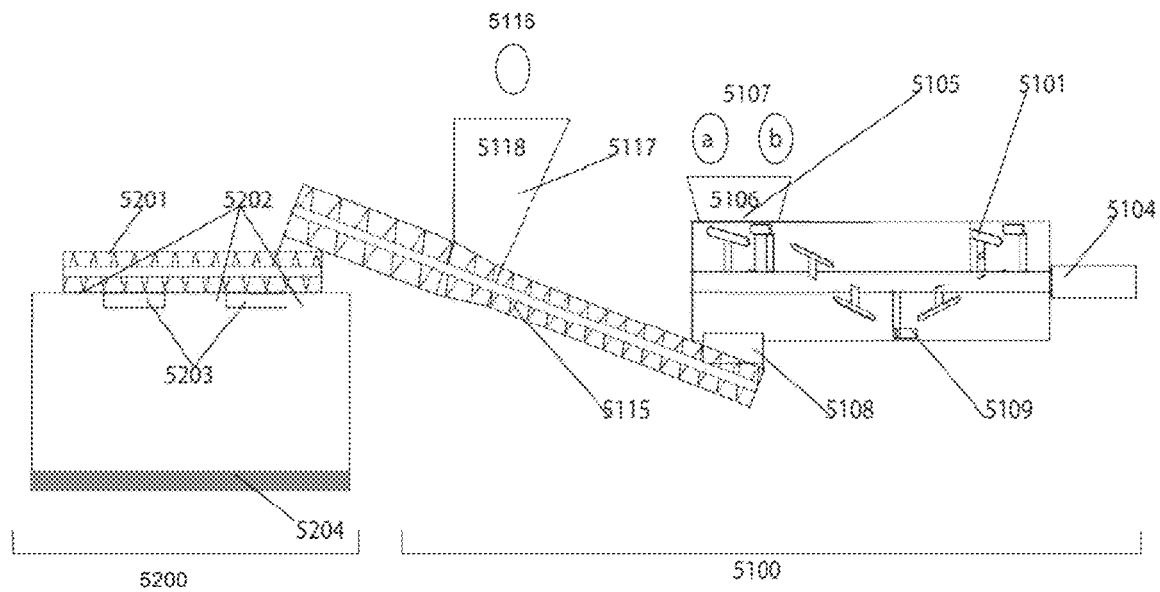
FIG. 7a shows an overview of the two first sections (initiation section 5100 and incubation section 5200) of the three-stage accelerated composting unit.
Figure 7B:
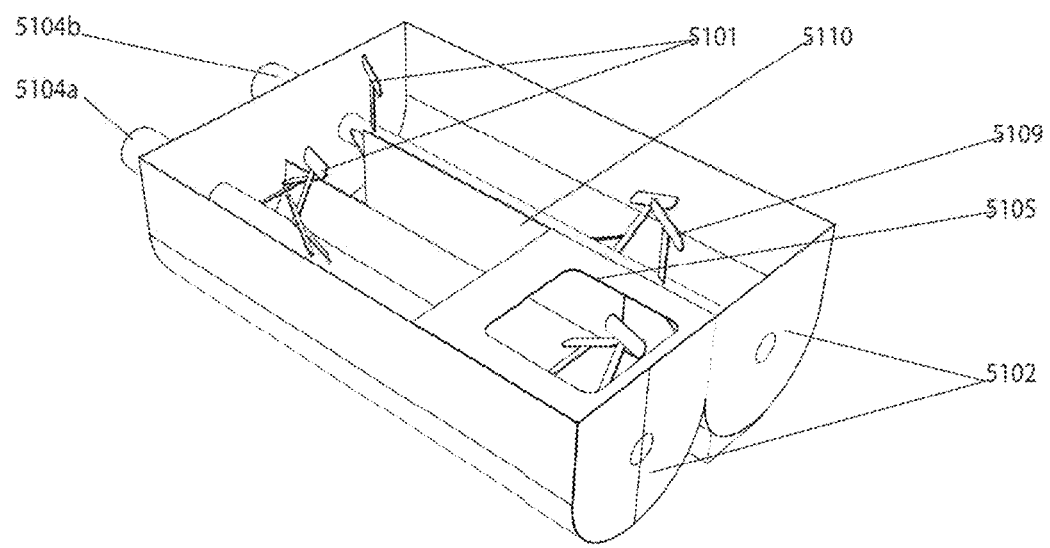
FIG. 7b shows a perspective view of the initiation section 5100 of the accelerated composting unit.

The system provides a complete organic waste treatment solution and comprises main modular units for i) pre-treatment of different streams of organic waste (1000, FIGS. 2 and 3), separation of such pre-treated organic waste to suitable components for further processing (2000, FIGS. 4 and 5), conversion of such components into fuels suitable for transportation purposes (3000, and 4000, FIG. 6) and iv) conversion of solid residues to high nutrition compost (5000, FIG. 7).

Individual modules and components of the system are designed for increased functionality beyond the current state of the art, and to minimize energy consumption and carbon footprint and maximize environmental and economic benefit.

The system provides a complete conversion of different waste material streams and combinations of these.

The different fuels that may be produced with this process are methane, ethanol and fatty acid methyl, ethyl and propyl esters (hereafter referred to as biodiesel).

These, and intermediate products, may also constitute raw material for the synthesis of other fuels or other valuable chemical entities.

The system as a whole is configured to ensure maximum synergy of individual components. The system is ergonomically and economically advantageous beyond the current approaches in environmentally attentive management of organic components of municipal and wider community waste.

It is designed to minimize both energy consumption and carbon footprint as well as to reduce the need for incineration and landfill disposal of organic waste.

The system is preferably installed at centralized municipal waste management facilities and it is comprised of modular units, the combination of which can be adapted to the specific requirements of each facility or site.

However, individual components or any combination of these may be installed at the point of generation of the respective waste or at any facilities treating, transporting or handling organic waste components, with the view of advantageous integration of individual components into existing waste management systems or as "stand alone" units where advantageous.

Components or their combination may also be adjusted to produce high value human or animal feed from individual waste streams alone or in combination with fuel production if preferable.

Thus the solution is flexible and can be adjusted to different compositions of waste streams at different points of their discharge and at different waste management facilities with the aim to maximize the ergonomic and economic benefits in each case.

In the current invention the organic waste streams are categorized as carbohydrate (C), fat (F) and protein (P) rich streams or any combination of these.

The system solution is a combination of modular pre-treatment, separation, and conversion units, each being preferably optimized to deal with a given C, F and/or P rich waste stream or any given composition of these.

In a preferred embodiment all organic components are combined and pre-treated combined, after grinding and homogenization as appropriate.

The pre-treatment process (1000), serves to affect degradation and hydrolysis of the lignin and cellulosic components (C) to more easily biodegradable material, and simultaneous hydrolysis of the protein component (P) to smaller peptides and amino acids, as well as hydrolysis and/or saponification of fats and oils (F).

The pre-treatment process in this preferred strategy is based on a continuous-flow steam explosion (1200, 1300). The steam explosion reactor is preferably operated under alkaline conditions, effectuating alkaline hydrolysis or saponification of all organic waste components, combined with the concurrent extraction of soluble hydrocarbons, amino acids or peptides as well as fatty acids and salts thereof.

When the steam explosion is driven in alkaline media, the aqueous alkaline extract and the solid substrate are subsequently lowered in pH with the $CO_2$ (S01) issuing from downstream anaerobic biogas production or from the fermentation unit (3000), where methane or ethanol is produced, respectively. This is achieved by constructing the pressure relief section of the steam explosion section of the pre-treatment units such that it adequately serves as an integrated $CO_2$ scrubbing section (1400) at the same time, comprises angular inlet and spiral inserts required for the direction of the substrate to a cyclone-like flow but at the same time directing and dispersing a fraction of the material inwards towards the centre of the pressure relief, carbon dioxide scrubbing section. Where a secondary scrubber is installed the effluent from the secondary scrubber is combined with the slurry from the primary scrubber prior to this the pH adjustment.

The pre-treatment process (1000) serves for the generation of a sterile, high nutrition solution or suspension with high bioavailability, suitable for methane production in an anaerobic digestion or alternatively for fermentation to produce ethanol. In addition to this, the pre-treatment process, when the steam explosion is driven under alkaline conditions, is engineered to serve as a scrubber for $CO_2$ removal (1400) from biogas produced downstream through anaerobic digestion (S01) of nutrients extracted from the solid substrate or for $CO_2$ removal (S01) from the fermentation of the substrate (extract) to produce ethanol, and/or for $CO_2$ removal from the flue gas exhausting from the boiler providing high-pressure steam for the process (U01, S02).

The utilization of the pre-treatment unit as a $CO_2$ scrubber serves three distinct purposes; i) removal of $CO_2$ from biogas produced downstream through the anaerobic digestion (S01) of the aqueous extract generated in the pre-treatment process or from the fermentation unit (S01) where ethanol is produced, as well as from the high-pressure steam boiler (U01, S02) in accordance with Eq. 1a, b and c;

$$CO_2 + H_2O \leftrightarrows H_2CO_3 (aq) \quad 1a$$

$$H_2CO_3 (aq) + NaOH(aq) \leftrightarrows NaHCO_3 (aq) \quad 1b$$

$$NaHCO_3 (aq) + NaOH(aq) \leftrightarrows Na_2CO_3 (aq) \quad 1c$$

ii) pH lowering and buffering of the substrate/aqueous-extract generated in the pre-treatment process, i.e., before it is subjected to three-phase separation (for the aqueous-extract to be utilized in methane production (S04) through anaerobic digestion or alternatively to alcohol generation through fermentation (3000), and iii) increase of the carbonate and bicarbonate concentration of the extract to enhance anaerobic conversion of carbon dioxide to methane through methanogenesis.

Consequently, the pre-treatment process as a whole simultaneously serves for sterilization, to increase the bio-availability of the organic waste material through structural rupture of compact fibre material, as a pre-hydrolysis unit, as an extraction unit and as a $CO_2$ scrubber. It is designed to increase the yield and the throughput of the biogas production beyond the current state of the art and at the same time to reduce the strain of the biogas refining to fuel grade methane.

After pH lowering through $CO_2$ scrubbing of the biogas and the resulting conversion of the $CO_2$ to carbonic acid, bicarbonate and carbonate (as outlined above in Eq. 1a-c), the liquid extract and the solid substrate are further pH adjusted in the conditioning section (2100) of the separation unit (2000) whereby pH adjustment, effectuates that alkaline salts of fatty acids are converted to free fatty acids and can be separated from the liquid phase through flotation (2200). The three-phase separation/conditioning process (2000) results in i) a fraction containing free fatty acids along with the remaining non-hydrolyzed fats and oils (S05), a fraction containing the aqueous extract with less than 15% suspended solids (S06), and the solid substrate (S07).

Alternatively, all fat and oil content in the form of free fatty acids and/or mono-, di-, and triglycerides is subjected to the anaerobic digestion together with other feed (S08).

As mentioned above, the three-phase separation unit in some embodiments comprises a separate fat/oil separation section and a separate solid liquid separation section. In a preferred embodiment the three-phase separation section is combined in one centrifugal decanter instrument. Exemplifying embodiments are described in detail in the Examples, with reference to FIGS. 4a-4c and FIGS. 5a and 5b, respectively and the working principles of the combined centrifugal decanter are detailed here below.

The combined centrifugal decanter of the present invention comprises a decanter house and a conical disc separation house, both mounted rotatable on a common bearing shaft. The houses can revolve independently. A screw conveyor inside the decanter house is rotatable around the same shaft. A central axially arranged stationary inlet feeds material into the decanter house. A stationary pump impeller is positioned between the decanter house and the conical disc separation house. The conical disc separation house encloses a dis separator that comprises a distribution disc and separation discs rotatable on an inner shaft. On the top of the separation discs is a top disc with an outlet pipe in its centre for the lighter phase and on the end of the conical separation house is an outlet pipe for heavy phase.

Working Principles of the Combined Centrifugal Decanter

The separator is based on two well-known separation principles, a screw conveyor decanter (decanter section) and a disc centrifuge (centrifuge section). The aim is to separate a solids fraction (liquid which consist of >25% dry matter), a heavy liquid phase (aqueous phase) and a light liquid phase (fat/oil phase) in one single machine.

Figure 5A:
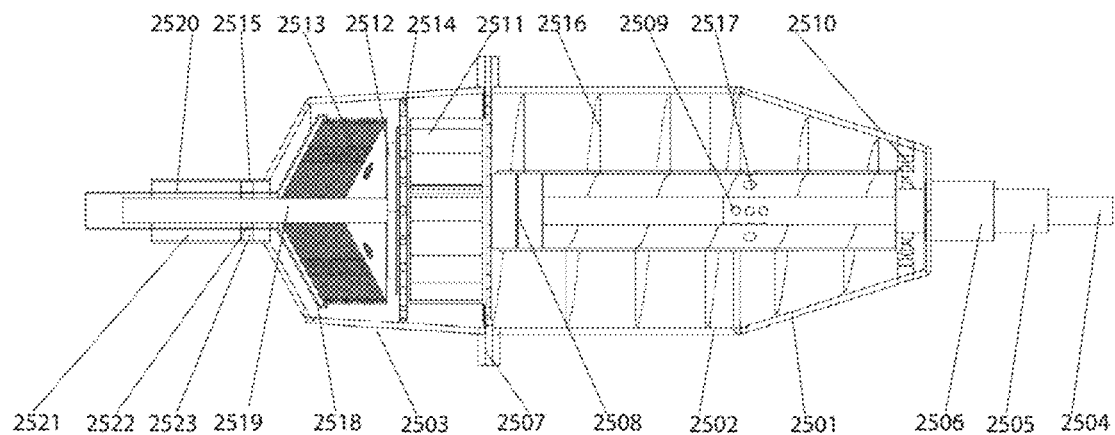
FIG. 5a shows an alternative embodiment of the three-phase separation unit where the three-phase separation is effectuated in a single apparatus combining the fat/oil and the solid liquid separation by applying a screw conveyor decanter and a disc centrifuge in one instrument, hereafter referred to as centrifugal decanter or centrifugal decanter unit or instrument.

The decanter house preferably rotates with at least 3.800 rpm speed and the screw inside rotate on a little lesser speed. Referring to FIGS. 5a and b, the raw material is pumped through inlet pipe (2504) and is distributed into the decanter through outlet holes (2509) and (2517). Because of the centrifugal forces the heaviest material (dry matter) is forced to the periphery of the decanter and will be transported by the means of the screw conveyor to the outlet of the decanter (2510). The liquid phase will locate in a drum shape inside the decanter and before the inner periphery of the water drum shape reaches the outlet holes (2510) the phase will enter the outer periphery of the stationary impeller (2511) which will convert the speed energy in the liquid phase into pressure energy and press the liquid towards the centre of the impeller where it will be pumped into the disc centrifugal part of the separator. From the centre it will enter the distribution disc (2512), which will distribute it equally up through the holes of the separation discs (2513). The separation of the liquid into heavy phase (e.g. water) and lighter phase (e.g. oil or fat) will take place on the surface of the separation discs and the capacity and separation rate depends on the total surface of the discs. The heavier phase together with rests of dry matter which may have come with it is pushed towards the periphery and fills the separator house and presses lighter phase material towards the centre of the centrifuge where the lighter phase reaches and is fed to the outlet pipe for the lighter phase (2520). The division/separation between light and heavy phase will depend on the difference on the special gravity of the two phases. The heavier phase will be pressed out through the outlet pipe (2521). The small amount of dry matter is pushed to the periphery of the centrifugal house and because of its conical shape and the centrifugal forces the dry matter moves in the direction to the decanter part of the separator. On the fixed plate (2514) and fixed plate (2507) there are small holes in the periphery, which allow dry matter together with small amount of heavy liquid phase to pass through and enter the decanter part of the separator. Solids matter is collected by the conveyor screw (2516) and transported to the outlet (2510) whereas liquid will circulate to the centrifuge again by the stationery impeller (2511) The small holes on the fixed plates cause a small internal leakage but the pressure drop in the holes secures that higher pressure will be established in the centrifugal part than in the decanter part and guarantees that a clean heavier phase will pass through the outlet pipe (2521) and the lighter phase through the outlet pipe (2520).

Where the fat and oil components are separated from the aqueous solution/suspension, these are subjected to esterification and/or trans-esterification as appropriate for the production of biodiesel, preferably in a continuous-flow biodiesel production unit (4000), which is a part of the present invention and can as well stand alone and operate independently. Alternatively, this continuous-flow biodiesel unit can be adapted to food- or feed grade production facilities where transesterification or esterification of fats constitutes an integral part of the process; e.g. the fatty acid ethyl ester production in the fish oil industry.

In a preferred embodiment the continuous-flow biodiesel production unit constitutes a one-step continuous-flow system (4000) adjustable to any combination of FFAs and glycerides and with high tolerance for water. Typically the system provides solid-state catalyst fixed on high shear stacked catalytic conversion plates and static turbulent plate mixers (4111 and 4131). However, the continuous-flow biodiesel production unit is also designed for conventional combination of homogeneous acid and base catalysed esterification or trans-esterification or combination of these in tandem, then requiring two reactors and eventual intermediate purification steps.

The aqueous extract from the three-phase separation unit is preferably subjected directly to thermophile anaerobic digestion for methane production or to fermentation for the production of ethyl alcohol.

In the current preferred embodiment the methane digester is combined with a fermentation system for the production of ethyl alcohol). In this embodiment the digester and the fermentation system constitute one production unit that may be used for methane or ethanol production interchangeably in response to production ergonomics, logistics and marked demand for the individual products.

The system may also be composed of dedicated units for either methane production through anaerobic digestion or ethanol production through fermentation.

Thermophile anaerobic digestion preferably takes place in a high rate anaerobic digestion system with low hydraulic retention time (HRT) but higher sludge retention time (SRT). Such systems include, but are not limited to Upflow-Anaerobic- and Expanded Granular Sludge Bed (UASB and EGSB Systems) as well as fixed film reactors and modifications of these, all of which can be configured as part of the present system.

Alternatively the methane production through anaerobic digestion may take place under mesophile conditions or combination of mesophile and thermophile conditions, and/or in low-load wet-reactors with high total solid content of up to about 30% or in dry fermentation with total solids higher than 30%.

Fermentation for the production of ethyl alcohol may also take place in any conventional fermentation setup and may include further enzymatic degradation of the substrate and further balancing with available sugar sources if advantageous.

The remaining solid substrate (S07) from the three-phase separation unit is transferred to stage one (5100) of a high-throughput, semi continuous, three-stage accelerated composting unit (5000). In stage one (5100), which serves as a mixing and initiation step the substrate is subjected directly to thermophile digestion, bypassing the mesophilic phase to accelerate the process. To achieve this, the sterile substrate from the three-phase separation unit (2000) is continuously mixed with seed compost, which is at its completion of the initiation process, i.e., at or close to the top of its thermophile stage. Further, the substrate from the three-phase separation unit is typically at a temperature in the range 40-50° C. at this stage, optimal for thermophile digestion also promoted under these conditions through the high content of readily digestible carbon provided through the pre-treatment process. The first phase, initiation phase, is maintained under continuous mixing, typically for a period in the range of 2-6 hours before being transferred to stage two (5200) under simultaneous addition of bulking material, which at the same time serves as additional carbon source.

In the stage one mixing and initiation step (5100), the fraction of the sludge removed from the anaerobic digestion may also be mixed into the compost substrate (S09). Present high bio-availability carbon sources that have not been subjected to anaerobic digestion may also be added to accelerate and balance the composting process. These may include, but are not limited to, glycerol (e.g. from the biodiesel production) (S10), flour, dough, fruit and other carbon rich disposal from the food industry and high sugar content solid disposal from other sources.

Where the high-nutrition extract from the pre-treatment process is used for ethanol production through fermentation, the sedimentation from the fermentation process may also be added to the mixing step of the composting unit (S09).

After the mixing and initiation step, the compost substrate is at or close to the peak of its thermophile stage and is transferred to a second stage that is without agitation but with active (forced) aeration and humidification (5200). In this second stage the thermophile phase is completed or almost completed, preferably in a period in the range of 24-96 hours before the substrate is transferred to the third stage (S13), the aging stage (U02).

Bulking material is dosed and mixed into the substrate in the transfer step from stage one to stage two (5100 and 5200). Preferably the bulking materials are wood chips with a size distribution in the range 10-50 mm acquired from the aging step of previous batches (S14), fresh or aged wood chips of other origin or any mixture of these.

Compensation for water loss through the aeration and humidity adjustment in stage two (5200) of the composting process may at least in part be achieved through adding effluent from the anaerobic digestion (S15).

In the third step, aging (U02), the substrate is subjected to maturing as appropriate, typically for the duration of three months to one year in open-air piles or other suitable and fitting arrangements.

In another preferred embodiment, high fat and oil component waste, including but not limited to, SHW, FIW, EOIW, and SwW, are treated separately in a rendering unit described in further detail below, for isolation of the bulk of the fat and oil components, as well as for volume reduction through water removal. The fat/oil component may in this configuration be subjected directly to biodiesel production and the water component may be discharged. The solid substrates remaining after fat/oil separation and water reduction are generally high-protein components, especially those resulting from SHW and FIW, but they may also contain an appreciable carbohydrate component e.g. from EOIW and SwW. These solid residues may be combined with other waste material. The combined streams are then subjected to alkaline-steam-explosion and alkaline hydrolysis with concurrent extraction of water-soluble nutrition components, as well as a subsequent pH adjustment and buffering with $CO_2$ scrubbing from the methane production as described above and shown in FIG. 3. The FFA, fat and oil fraction is subjected to esterification and transesterification as described above.

EXAMPLES

The following establishes specific embodiments of the invention and should not be taken as limiting. The overall system constitutes a system and technique for in-line conversion of all organic components of municipal and larger community waste, to fuels suitable for transportation purposes and conversion of all remaining solid fractions generated in the process to compost.

The system, for which a schematic flow diagram overview is shown in FIG. 1b, is designed to maximize synergy between individual components beyond the current state of the art, to minimize energy consumption and carbon footprint and maximize environmental and economic benefit. Individual components of the system are designed for increased functionality beyond the current state of the art, and to minimize energy consumption and carbon footprint and maximize environmental and economic benefit.

In this exemplified embodiment the system comprises
  a continuous-flow alkaline steam explosion reactor and integrated $CO_2$ scrubbing unit (1000),
  a conditioning and separation unit (2000 or 2500),
  a methane production unit, alternatively combined with or substituted by an ethanol production unit (3000),
  a continuous-flow biodiesel production unit adjustable to any free fatty acid and glyceride composition and with high water tolerance (4000) alternatively substituted with other continuous-flow configurations or conventional batch systems and
  a quasi-continuous composting unit (5000).

Optionally, the system is also furnished with a compact wet-rendering unit for separate treatment of high fat and oil component waste (6000).

Combined, the system provides a complete conversion of different waste material streams comprising organic waste and combinations of these, to fuels suitable for transportation purposes and the conversion of all solid residues of the processes to compost.

Waste material streams suitable for conversion in the process include, but are not limited to; household waste (HHW), slaughterhouse waste (SHW), food industry waste (FdIW), fish industry waste (FhIW), waste from the vegetable oil and the fish oil industry (OIW), sewage sludge, sewage grease and oils (SwW), agricultural waste such as wheat-straw or other straw, rice husk, soybean curd residue, and grass and animal manure (AcW), as well as garden waste (GW) and waste wood (WW).

Products from the process may be combinations of:
  methane, biodiesel and compost,
  ethanol, biodiesel and compost or
  one of these fuels and compost.

Continuous-Flow Alkaline Steam Explosion and $CO_2$ Scrubbing Unit)

The Continuous-flow alkaline steam explosion and $CO_2$ scrubbing unit comprises a grinding and homogenizing section (1100), a wetting and mixing section (1200) also referred to as conditioning section (or specifically as pretreatment conditioning section), high-pressure heating-retention section (1300) and an explosion relief and $CO_2$ scrubbing section (1400). The explosion relief and $CO_2$ scrubbing section of the steam explosion and $CO_2$ scrubbing unit serves as the pressure relief section of the steam explosion section and at the same time as absorber for $CO_2$ scrubbing of the methane/$CO_2$ mixture from the anaerobic digestion (S01) or alternatively the $CO_2$ from the fermentation process (S01), as well as the $CO_2$ from the flue gas (S02) from the systems steam boiler (U01).

The wetting and mixing section (1200) preferably constitutes a top fed conveying mixer (1201) equipped with an integral wetting armature (1202) preferably in a top-down spraying configuration.

The waste stream comprising organic waste to be processed and which has preferably been shredded at the mentioned upstream grinding and homogenisation section, is fed into the far end of the wetting and mixing section (1203) and conveyed under mixing towards its exit point (1204). During this step the solid substrate is wetted (1202) to achieve the desired water content (S22) optimal for the steam explosion process and at the same time pH adjustment is achieved.

For alkaline steam explosion integrated with $CO_2$ scrubbing as described in this preferred embodiment, the aqueous solution is alkaline, preferably through solution of sodium or potassium hydroxide (S23) added to the wetting water in a liquid/liquid mixer (1205).

The steam explosion unit may also act as a stand-alone unit or in other combinations and may be driven with pH neutral or acidic feed, with non-pH adjusted feed or with feed mixed with any other additives suitable for promoting the intended processes.

The exit port of the wetting and mixing section (1204) is connected vertically to the steam explosion section via a rotation-dosing valve (1206) and a high-pressure, rotating valve (1301), which may advantageously be in a positive displacement configuration.

At the exit point of the wetting and mixing unit (1204), the substrate enters the rotating dosing valve (1206), which doses the substrate into an ambient pressure compartment of the high-pressure rotary valve (1301). The rotating dosing valve serves to avoid overload of the high-pressure rotary valve causing unnecessary strain on the high-pressure sealing. After loading at ambient pressure, the high-pressure valve rotates to a sealed position where it is brought up to the desired pressure (preferably in the range 10-30 bar, typically about 1 bar above that of the heating-retention unit) and temperature through steam injection (typically 180-250° C.) (1302). The high-pressure rotating valve then rotates further to a vertical placement) above the entrance port of the heating-retention unit.

High-pressure steam is provided by a boiler (U01, S18), driven by fuels produced in the overall-process. This may be pure methane or any methane/$CO_2$ mixture, from the anaerobic digestion unit (S19), biodiesel (S20) or any mixture of fats, oils or fatty acids prior to their esterification or trans-esterification (S21).

Assisted by the differential pressure and gravitation the now pressurized chamber is discharged into the heating-retention section (1300) of the steam explosion unit before rotating further into a second sealed position where pressure is released (1303).

Pressure strain on the rotation-valves may be reduced by using rotation-valves with more compartments and gradually increasing the pressure in individual compartments in the inlet system, lowering the differential pressure between these.

In a positive displacement configuration applied in some embodiments, pressurization and depressurization is assisted by the respective chamber volume variation through the rotary cycle.

In the high-pressure heating-retention section (1300), the loaded substrate is conveyed from the loading point to the exit point by means of an adjustable speed screw conveyor (1304) allowing the retention time to be continuously adjustable over a wide time range.

The unit is equipped with steam injection ports (1305) to achieve the appropriate pressure and temperature and for its maintenance by make-up injections. Two such injection points are shown as examples in FIG. 2 (1305).

The exit port of the high-pressure heating and retention section is connected vertically to a rotating dosing valve (1306) and a high-pressure rotary relief valve (1307). At the exit point, the substrate is conveyed by the rotating dosing valve (1306) to a compartment of the high-pressure rotary relief valve, which at that time-point faces the exit port of the high-pressure heating and retention section).

The rotary valve (1307) then rotates to open the pressurized compartment to ambient pressure, enabling the steam explosion, before rotating to a re-pressurization position, this compartment equipped with a steam injection port. From this position the compartment rotates back to the fill position.

In this configuration heat efficiency is maximized by dynamic synchronization of the steam injection into the high-pressure feeding rotary valve, the heating-retention section and the re-pressurization section of the high-pressure rotary relief valve. With all injections controlled individually. This is done in response to variations in pressure and temperature caused at the relief and entrance side and through heat loss. Pressure and temperature is monitored continuously along the high-pressure heating and retention section supplying individual data along the section (DS01). This data is feed to the P/T processing unit (1309) supplying control signal to the steam injection ports (DS02). These are synchronized to this signal along the high-pressure heating and retention section to maintain close to constant conditions. Additional signal (DS02) is supplied to adjust the speed of the rotating conveyor (1304). Three P/T monitoring points are shown as examples in FIG. 2.

In some embodiments it is found advantageous that the extrusion port of the exit rotary valve is partially obstructed with suitable constructions to utilize the mechanical force in the steam explosion for further mechanical surface roughening/shredding of the extruding material. This is exampled in FIG. 2 by a shredder teeth arrangement (1310) intended for additional surface roughening of wood chips.

Where the steam explosion device is operated under alkaline conditions and constitutes an integral part of a $CO_2$ scrubbing unit, the upper part of the $CO_2$ scrubber (1400) is in a cyclone type configuration, designed to promote perpendicular dispersion towards the centre of the scrubber for optimal contact of the alkaline material with a counter-flow of the $CO_2$ rich exhaust.

Figure 3A:
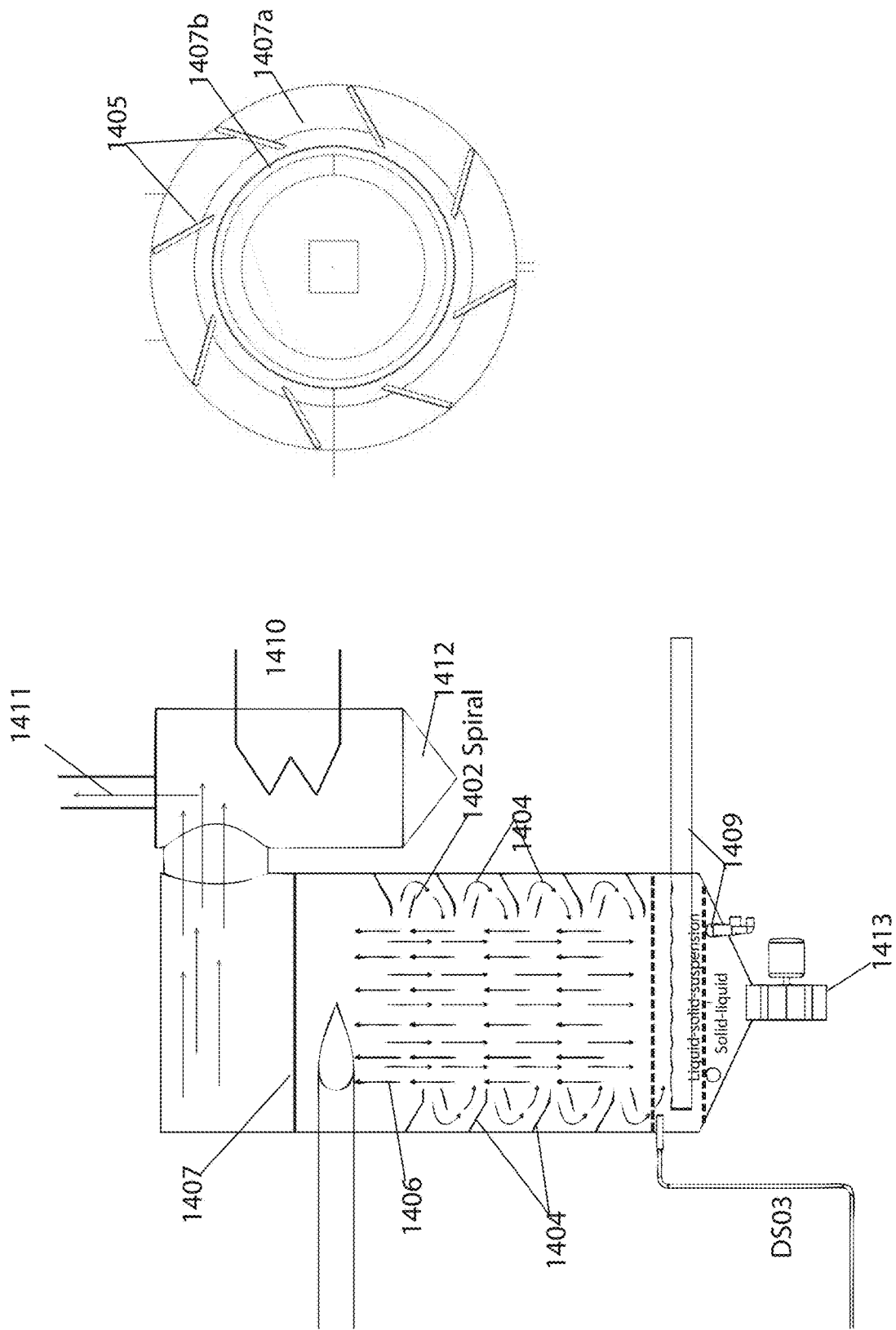
FIG. 3a shows a schematic illustration of a version of the carbon dioxide scrubbing section of the pre-treatment unit.
Figure 3B:
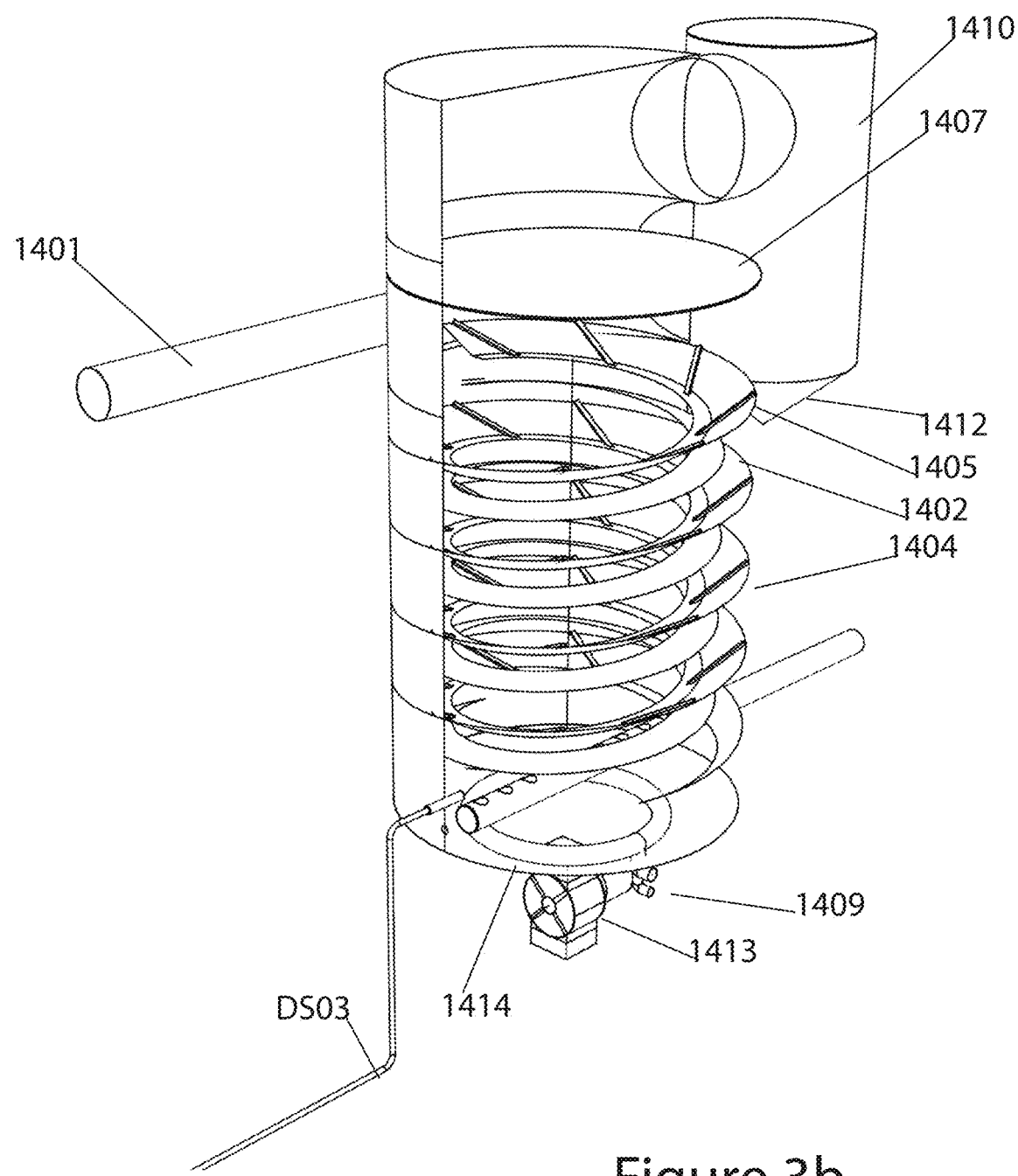
FIG. 3b shows a perspective exploded view of the carbon dioxide scrubbing section of one embodiment of the pre-treatment unit.
Figure 4A:
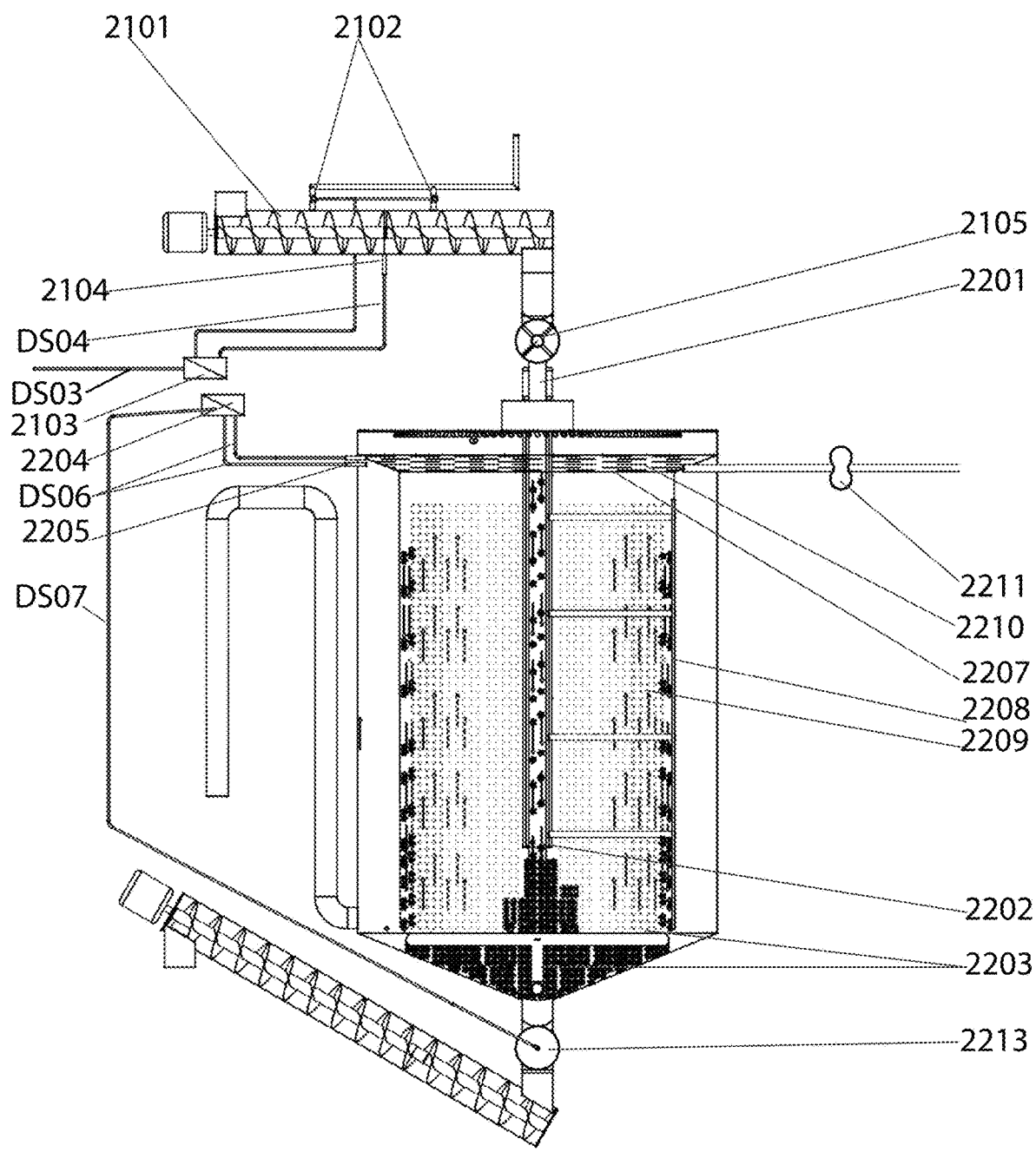
FIG. 4a shows a schematic illustration of the main sections of one embodiment of the separation unit, the top portion shows the conditioning section, which leads to the fat/oil separation section, which comprises a central coaxial tube within a vertically arranged tank. At the bottom is a solid/liquid separating conveyor.
Figure 4B:
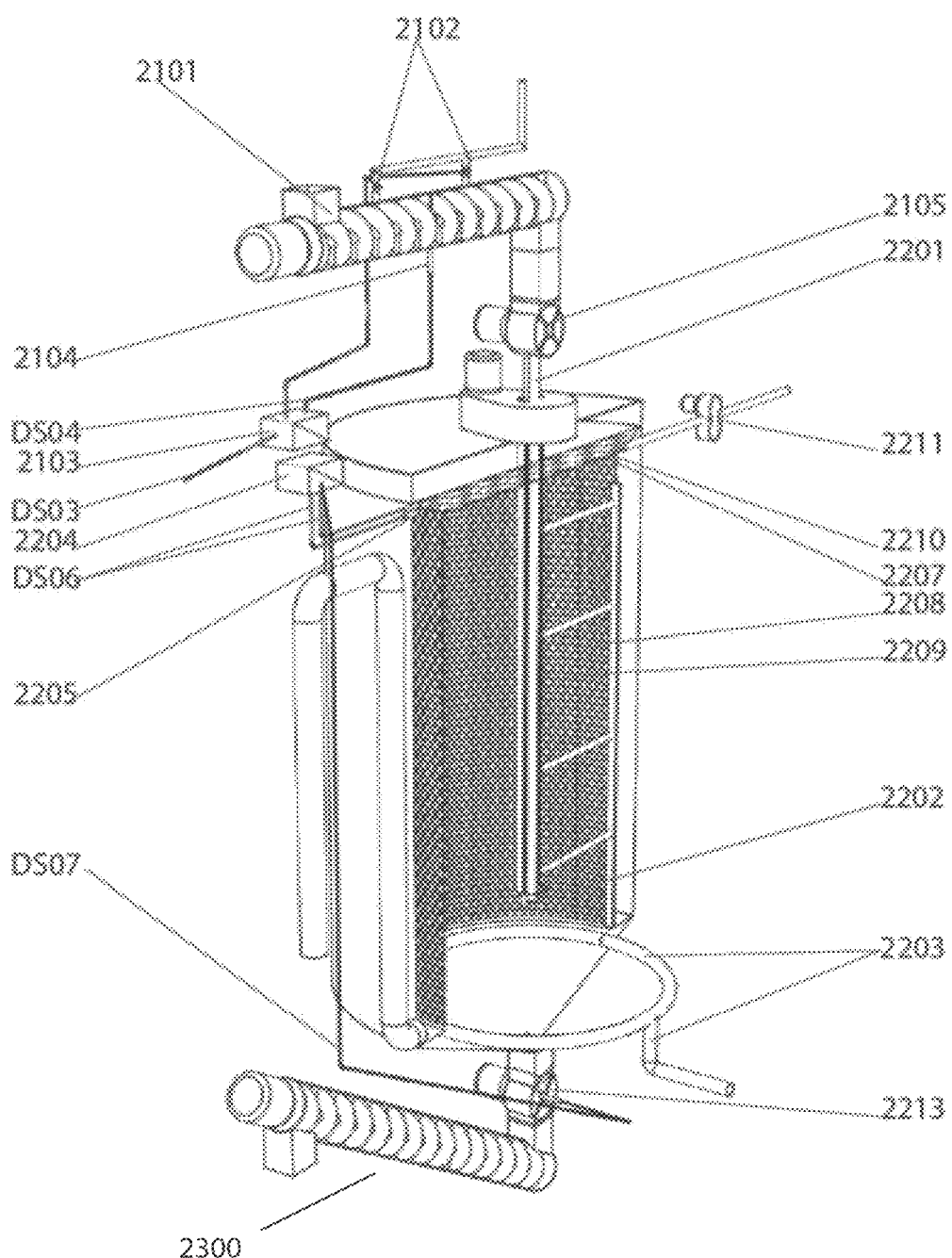

The loaded chamber of the high-pressure rotary exit valve is discharged under an appropriate angle (1401) at the upper part of the combined relief and $CO_2$ scrubbing section (1400) directing the high-speed steam/substrate downwards on to a cyclone type spiral configuration (1402) with clearance from the inner walls of the primary scrubber compartment. An exemplary configuration is shown in FIG. 3. Through the high velocity of the discharging material the heavier fraction and condensed steam is forced towards the inner wall of the scrubber/cyclone confinement with a downward velocity component provided by the initial angle of entrance (1401). This fraction is caught by a corrugated spiral-plate below and parallel to the cyclone spiral with wall clearance (1404).

The corrugation (1405), the downward slope of the spiral plate (1404) and the downwards velocity of the substrate/condensate partly directs it along the surface of the lower spiral plate (1404a) towards the centre where it is dispersed by an upwards directed protrusion (1404b) terminating the inner side of the spiral plate, thus enhancing the contact of the alkaline suspension with the counter flow of CO2 rising up through the scrubber. The dispersing substrate/condensate (1406) falls down the centre of the scrubber/cyclone confinement, along with steam condensing in the central region and at the demistifier (1407), to accumulate in the settlement region of the scrubber/cyclone.

Alternatively, the settlement region is equipped with a cooling spiral or other heat exchange elements to partially recapture the heat from the steam explosion, thus lowering the substrate temperature and preheating the water input for the steam generation boiler providing the system. Such cooling elements may also be installed or extend to the upper section of the scrubbing unit and are preferably in contact with the guiding spirals to effectuate rapid cooling of the substrate already in the upper section of the scrubber.

The horizontal/angled part of the discharge tube (1401) is separated from the gas void section below the gas exhaust port with a demistifier mesh (1407).

The $CO_2$ containing exhaust (S01 and S02) is fed from the bottom through a micro-bubble dispenser (1409). This is preferably through aspirators a tilted, lateral arrangement, driven by circulation of the low solid aqueous suspension taken from the upper part of the suspension section. In this arrangement the aspirators serve at the same time for agitation of the liquid solid suspension, achieving consistent composition at the exit port of the section and avoiding clogging. Alternatively, $CO_2$ containing exhaust (S01 and S02) is fed through a micro-bubble or other, passive, dispersion set-up.

The $CO_2$ containing exhaust protrudes through the substrate settlement region and is in further contact with the alkaline adsorbing suspension in the upper, central part of the condensation section of the scrubber before exiting with the dry fraction of the steam through a condenser (1410) at the gas exit port of the condenser (1411).

The remaining steam is removed in the condenser (1410) with the $CO_2$ lean gas ($CH_4$ when scrubbing $CO_2/CH_4$) exiting the gas exit port (1411) and the condensate exiting the drain port (1412). The heat of condensation is used to preheat the aqueous fed for the wetting unit.

Alternatively, the gas exit port (1411) leads to a secondary scrubber that may be operated under elevated pressure and at lowered temperature. The secondary scrubber is fed with the preferably cooled liquid fraction of the primary absorber scrubber in a conventional spray configuration from the top and with the CO2 lean exhaust from the primary scrubber from the bottom.

The scrubbing section of the pre-treatment unit advantageously serves to remove $CO_2$ from the raw $CO_2/CH_4$ mixture produced in the anaerobic digestion process or the $CO_2$ produced in the fermentation process and/or to remove the $CO_2$ from the flue gas from the steam boiler providing the system (U01).

The liquid-solid suspension is periodically released as fractions through a discharge valve at the bottom of the relief and CO2 scrubbing section (1413). These fractions are subjected to the conditioning and separation unit (2000) and their collection is synchronized with the discharge from the steam explosion unit to achieve continuous load conditions in the process.

Three-Phase Separation Unit

The three-phase separation unit (2000, FIGS. 4 and 5) is composed of, i) closed conditioning section (2100), continuous fat/oil separation section (2200), iii) a liquid/solid separator (2300), and iv) a fat/oil buffer tank (2400) feeding a centrifugal purifier (2450). In this preferred embodiment where the system is presented as whole, this unit serves to separate and clarify the fat and oil content from the pre-treated organic waste and to separate the remaining aqueous and solid phase.

The solid fraction preferably maintains adequate humidity for composting (in the range 40-70%) and the liquid phase contains adequate solid suspension to support the anaerobic methane production (10-15%), or alternatively ethanol production through fermentation (3000).

The conditioning and fat/oil separation sections (2100 and 2200) comprise a conditioning section (2100) which is fed through a rotating or other suitable valve at the discharge port (1413) of the pressure-relief and $CO_2$ scrubbing section of the pre-treatment unit (1400). Continuous agitation in the conditioning section is provided, preferably through a conveying mixer (2101), and the pH of the substrate is adjusted by acid injection through two spraying armatures (2102). The spraying armatures serve for controlled addition of acid and/or further aqueous solutions to the conveyed substrate for pH adjustment under active mixing. In this preferred embodiment, pH adjustment proceeds in two stages through spraying units (2102) installed through the top of the conditioning section (2100). Both spraying armatures (2102) may be mounted perpendicular to the conveying direction from the top of the conditioning section (2100). The first is installed at the far end just after the entrance port. The second spraying armature is installed about ⅔ downstream. In operation, pH readings (DS03) are fed to the control of the spraying armature (2103) from the sediment/condensation part of the $CO_2$ scrubbing section (1414) of the pre-treatment unit (1400). This reading controls the release from the first armature (2102). A second reading (2104, DS04) is delivered to the control (2103) of the spaying armatures from about half way downstream of the mixing and conditioning unit. This reading controls the second spraying armature.

The condition section (2100) of the separation unit, discharges continuously in to its fat/oil separation section (2200) through a discharge valve (2105), in to a central, cylindrical tube (2201). The exit of the central cylindrical tube (2202) is maintained below the micro-bubble injection ports or nozzles (2203) in the fat/oil separation section of the separation unit.

The surface level in the fat/oil separation section is maintained through active control (2204, DS07) of its discharge in response to a liquid level reading (2205, DS06). For promotion of fat and oil separation from the aqueous and solid fraction, micro-bubbles are injected at the bottom of the oil/fat separation section, above the central feeding tube through ports (2203). In a preferred embodiment the micro-bubbles are injected perpendicular to the feed tube in a saturated stream of water generated by a centrifugal pump, or through aspirators as shown in FIG. 4 (2203). Water is provided from the centrifugal purifier (not shown) and/or the upper aqueous section of the fat/oil separator (2207). This provides convection perpendicular to the micro-bubble rise and the sediment fall (2208). Where advantageous the micro-bubble generation may also be achieved by pressurized air injection through perforated armatures at the bottom of the fat/oil separation section. The rise of the micro-bubbles promotes the separation of fat and oils from the aqueous/solid suspension through flotation and assures for appropriate material convection and additional perpendicular convection where air-saturated water injection is applied (2208). To constrain convection and mixing in the fat/oil section of the fat/oil separation unit, this section is preferably separated from the aqueous suspension section with two meshes (2209) placed vertically at about ¾ of the height of the separation unit. The meshes are preferably spaced by about 50 mm and rotated 45° with respect to their principle mesh line.

Fat and oil continuously accumulates at the surface (2210) and is continuously drained through an automated, adjustable surface pump (2211) or alternatively through an overflow drain pocket. The oil/fat fraction removed is pumped to a buffer tank feeding the centrifugal purifier where it is cleared from remaining water and solid residues. The cleared water fraction is fed back to the micro-bubble injector, where appropriate or fed to the anaerobic digestion or fermentation unit. This may proceed anywhere along the feed line from the solid liquid separation unit or directly where beneficial. The purified fat and oil fraction is subjected to esterification or transesterification as appropriate for the production of biodiesel in the biodiesel unit (4000). The discharge of the aqueous suspension and the substrate, from the fat/oil separation section to the solid liquid separation section of the separation unit is synchronized with the surface level with active control of the discharge valve (2213, DS07).

Figure 4C:
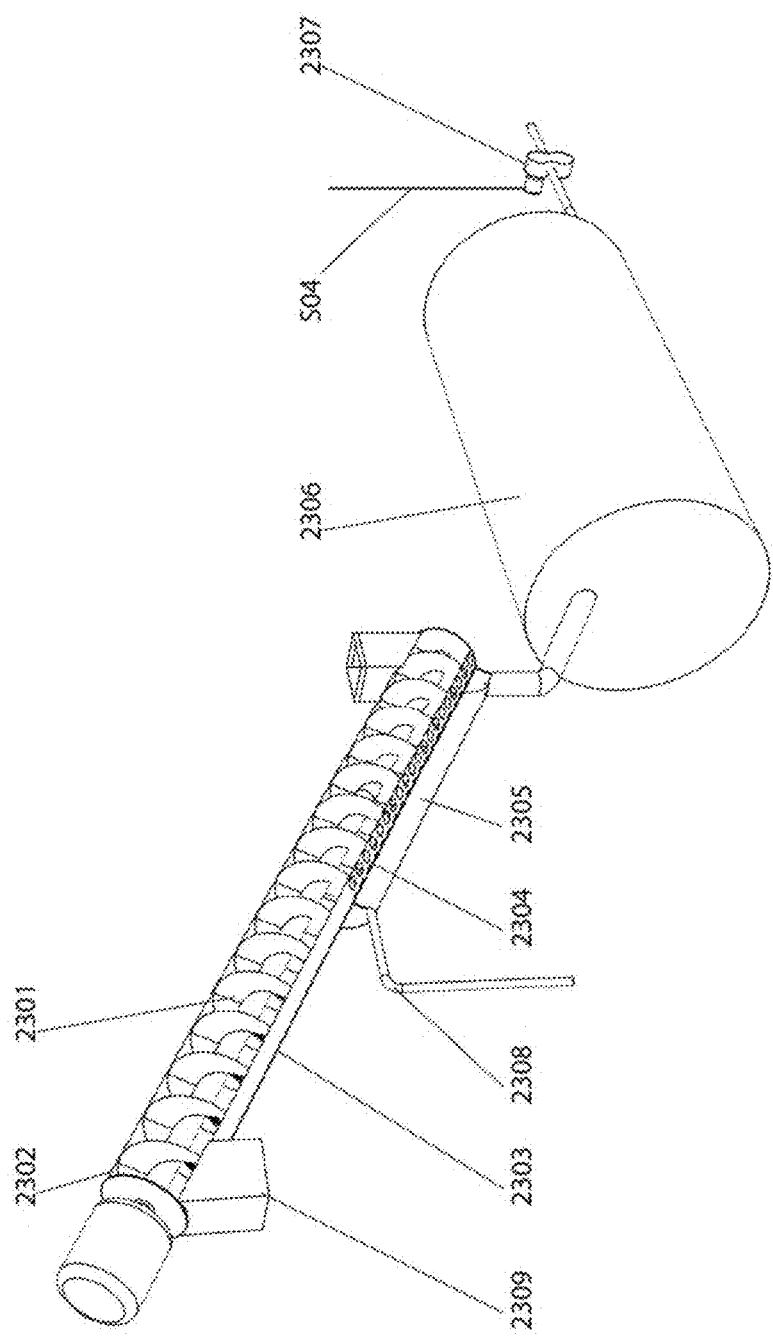
FIG. 4c shows a perspective view of the solid/liquid separating conveyor from FIGS. 4a and 4b, and a collection/buffer tank, for receiving liquid material from the liquid/solid separator.

The solid liquid separation section is in this embodiment composed of a compressing screw conveyer (2301) with a compressing zone at the top section (2302), as illustrated in FIG. 4c. The screw conveyer is embedded in a cylindrical housing (2303), with the lower 20-60% section comprising a perforated bottom plate (2304) constituting drainage for the liquid suspension. The complete separation unit is adjustably tilted to attain optimal performance with respect to solid/liquid separation.

The perforated section of the screw conveyer housing is exchangeable for maintenance and is adjustable in length and perforation size and density to allow adjustability of particle size and quantity of the solid component in the aqueous suspension.

The aqueous suspension is drain from the conveyer along a chute confining the perforated section of the conveyer housing (2305). It exits the solid liquid separation section at its lower end to accumulate in an intermediate buffer tank (2306) from where it is pumped to the digestion or fermentation unit or to further storage as appropriate (2307). A flushing water nozzle is installed at the top end of the chute for rinsing and cleaning as appropriate (2308). The solid fraction exits the upper end of the screw conveyer (2309) from where it is transferred to the three-stage composting unit (5000).

Alternative Separation Unit, Centrifugal Decanter 2500

Figure 5B:
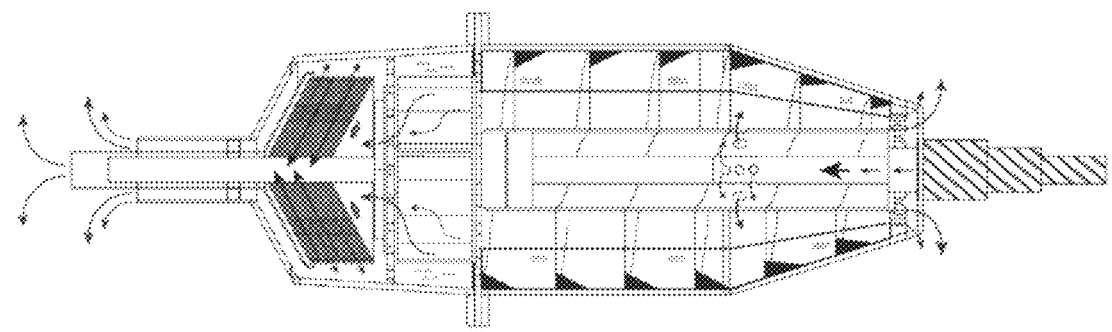
FIG. 5b shows the three-phase separator unit from FIG. 5a, further detailing material flow in the separation process.

FIGS. 5a and 5b illustrate an alternative embodiment that has been developed for the present invention. A decanter house (2501) (2502) and conical disc separation house (2503) are joined and held in place by bearings in the unit nave (2506) and bearing shaft (2515). The houses revolve at least about 3800 rpm rotated by a main drive having a wedge belt drive (not shown). Screw conveyor (2516) rests on bearings on a bearing hub for the decanter screw conveyor (2505) and hub for the inner bearing (2507). The screw conveyor (2516) rotates on less speed than the housing and is driven by an auxiliary drive with a wedge belt drive (not shown). An inlet pipe (2504) is stationary and rests on a positioning trestle in the inlet end and on positioning bearings inside the decanter (not shown). The inlet pipe is equipped with outlet holes (2509) for the material to enter into the decanter through the outlet holes (2517) on the screw conveyor (2516). On its other end the inlet pipe is joined to a stationary pump impeller (2511). The inlet pipe and the stationary impeller rest on bearings (not shown), which are fixed on a plate for distribution ring (2514). An inner shaft (2519) is fixed to distribution disc (2512) and separation discs (2513) are located on inner shaft (2515). On the top of the separation discs is top disc (2518). In the center of the top disc (2518) is an outlet pipe (2520) for the lighter phase and on the end of the conical separation house (2503) is an outlet pipe (2521) for heavy phase. The outside of the outlet pipe for heavy phase (2521) forms bearing hub (2515) with supports for the inner shaft (2522) and for outlet pipe (2523).

Continuous-Flow Biodiesel Reactor, Unit 4000

The fat/oil component from the fat/oil separation of the separation unit is composed of a substantial fraction of free fatty acids, typically in the range of 30-60% with the rest being mono-, di- and tri glycerides resulting from incomplete saponification in the pre-treatment step. Where the fat/oil component is separated from particular fat-rich waste streams in the compact rendering unit (6000) before the alkaline steam explosion, the FFA fraction is typically 10-30%.

In a preferred embodiment the fat/oil component from the centrifugal purification is subjected to single, or multiple stage esterification of FFAs and transesterification of glycerides in a modular flow reactor (4100) designed to be adaptable to any FFA and glyceride composition and comparatively high water content. The continuous-flow reactor is explicitly constructed to allow for flexible, effective and economical conversion of low grade feed stock of variable composition ranging in FFA and glyceride ratio from 0-1.

The biodiesel unit of the invention provides a continuous-flow reaction system applicable to; i) a wide range of throughput and catalytic contact time requirements, ii) a large pressure and temperature range and efficient heat transfer, iii) high degree of flexibility in catalyst composition and structure, iv) high degree of flexibility in constellation, maintenance and catalyst regeneration. Said continuous-flow reactor is modular and is composed of three principal components; i) corrugated contact plates with one side coated with catalytic material (4110), ii) spacers with catalytic and flow perturbing inner surface (4120) and iii) static mixers with catalytic surfaces (4130).

The reactor is equipped with an inlet system constructed to allow for effective mixing of the reactants prior to or during the injection in the reactor and alternatively additional adding of homogeneous catalysts, and addition of co-solvents where appropriate. Such co-solvent is preferably methyl esters produced in the process and partly recirculated, promoting the formation of a homogeneous reaction mixture of methanol, glycerides and FFAs. An example of the utilization of the pre-mixer is shown in FIG. 6a (4101). In this example sulphuric acid is premixed with methanol as homogeneous catalyst or for activation of a solid-state catalyst. This serves at the same time to harvest the solvation energy released in this process. In another pre-mixer the free fatty acids and glycerides are mixed with comparable fatty acid methyl esters, that may be produced in the process, or other co-solvent. The respective blends are then mixed in a third pre-mixer.

In a preferred embodiment the continuous-flow biodiesel reactor, shown as complete in FIG. 6a, is configured to allow for esterification of FFAs and transesterification of glycerides in a single step.

In the current embodiment the continuous-flow biodiesel production unit comprises corrugated plates (4110) coated on one side with a solid-state catalyst (4111) providing a catalytic surface. Alternatively, the corrugated contact plates comprise a surface layer on one side with immobilized catalysts, preferably enzymes, for catalytic conversion of free fatty acids and/or transesterification of glycerides. The plates are preferably stacked with alternating two coated surfaces facing each other and two non-coated surfaces facing each other. Any other sequence of stacking is optional if advantageous. The spacing between plates is adjustable through spacers (4120) with flow disrupting inner surfaces for enhancing turbulent flow and efficient mixing at the verge of the reactors flow regime. Distance between catalytic contact plates can be configured as desirable by the appropriate choice of spacer's width.

Preferably the inner surfaces of the spacers are also coated with the appropriate solid state or enzymatic catalyst (4121). The spacers are with sealing gaskets and confine the void between individual corrugated contact plates. In this configuration the void between the non-coated surfaces provides a channel for a heat exchanging media such as steam, oil, water, coolant etc. The void between the catalytic surfaces provides the reaction zone of the continuous-flow reactor (FIG. 6b). Alternatively, static mixer plates (4130) are installed between the catalytic contact plate with spacers now defining the void between the static mixer plate and the catalytic contact plates bracketing these (FIG. 6c).

The static mixers are preferably coated with the same catalyst as the contact plates (4131). Thus such static mixer increase the extent of the catalytic surface, allows for better control of the macroscopic flow through the reactor and provides effective mixing and exchange of material at all catalytic surfaces. For clarity a non-limiting example of a cross section through a static mixer section of a reaction cell is shown in FIG. 6d along with reactant flow lines (4133).

In this example partial flow is directed from the entrance compartment by angled, counter-flow slits terminated with shorter counter flow fin at the exit compartment side of the mixer. Restricted direct flow in to the exit compartment ensures a net fluid drag towards the exit port of the respective reaction cell (downwards in FIG. 6d) and ensures for turbulent mixing in the exit section of the reaction cell.

Further net fluid drag towards the exit port and increased turbulence, may be achieved through additional restricted flow slits directed in the principal flow direction provided between the counter flow slits. An example of this configuration providing two restricted flow paths along the principal flow direction is illustrated in FIG. 6d. The respective voids are connected in series to allow continuous-flow through the reaction zone and the heat exchange zone respectively. These flow regimes may be in parallel or in a counter flow configuration depending on the desirable heat gradient. The alternating contact plates and spacers and static plate mixers are stacked in the appropriate order on lateral tracks and compacted by rigid end-plates on independent sliders. The confinement between the end plates allows for high lateral operation pressure that is only limited by the specifications of the end plates.

For high- or ultra-high-pressure applications, exceeding the transversal tolerance of the gaskets, the continuous-flow biodiesel reactor is encapsulated in a differential pressure equalizer. The differential pressure equalizer encompasses a high-pressure sealed (4102) casing and serves primarily to reduce the transversal pressure strain on the reactors gaskets. The inlet and exit ports of the reactor (reactants and thermal fluids) extend outside the casing though a high-pressure tubular sealing (4103) or other high-pressure sealing.

The reactant feed is supplied with a high-pressure liquid pump (4104a), preferably air driven, placed after the static pre-mixer (4101) and the pressure is controlled through a back-pressure regulator at the exit port of the reactants conversion path. Similarly, the thermal liquid is supplied with a high-pressure liquid pump (4104b), preferably air driven, and the pressure is controlled through a back-pressure regulator at the exit port of the thermal media path (4105b). The pressure buildup in the thermal section and in the conversion section during start-up, its maintenance and its reduction when operation is halted, is actively synchronized with readings from both back pressure regulators being feed to a control unit (4106) synchronizing the high-pressure pumps for the thermal media and the reactant feed (DS12 a and b to 4104 a and b).

In operation within the differential pressure equalizer, the casing is maintained at a pressure comparable or slightly lower than the operation pressure of the reactor. Preferably the reactant pressure, the thermal media pressure and the casing pressure is achieved and maintained with air driven, high-pressure or ultra-high-pressure liquid pumps (4104 a, b). The pressurization liquid is preferably fatty acid methyl esters produced in the process or with comparable chain length to that of the produced biodiesel, but may also be other media, preferably inert and of low compressibility.

Alternatively, the heating section can be split into two or more heating zones, where separate zones may be heated with different media, e.g., oil and steam. Such separation may also serve to minimize heat gradient by parallel injection of e.g., the same heating media into different zones of the reactor system. Similarly, the reaction zone may be stacked to provide different section with distinctly different reaction conditions. For biodiesel production these may e.g., constitute a first section where the catalytic surfaces are primarily tailored for FFA esterification and a second section where the catalytic surfaces are primarily tailored for trans esterification of the glyceride fraction of the feed. These may e.g. be acidic and basic solid-state catalysts respectively or different enzymatic catalysts. Where advantageous these sections may further be separated by ion exchanging sections or dehydration sections, where the dehydration or ion exchanging material is immobilized on the surfaces of the respective, stackable plates and may be regenerated through heat or chemical treatment without dismounting the reactor. This may be of particular advantage where the activity of the catalytic surfaces is boosted by parallel injection of a homogeneous catalyst or media for maintaining the activity of the catalytic surface. An example where such media may be advantageous is the use of sulphated zirconium oxide or other sulphated metal oxides. Here a co-injected sulphuric acid may at the same time serve as a homogeneous catalyst and serve to maintain the activity of the catalytic surface. Similar situation may apply with respect to co-injection of alkaline hydroxides or other basic media where basic catalytic surfaces are applied.

Alternatively, the reactor may be divided into sections where it is advantageous to run esterification of FFAs and transesterification of the glyceride fraction separately. In such configurations one or both sections may be run with homogeneous catalysts with adequate purification/conditioning as intermediate steps. These may include but are not limited to flash evaporation, dehydration or ion exchange.

Semi-Continuous Composting Unit (5000)

The semi continuous composting unit (5000) comprises a three stage accelerated composting process, in which the first step constitutes an accelerated initiation step (5100), tolerant towards low C:N ratio through carbon content of high digestibility and bypassing the mesophilic phase through high initial substrate temperature, high seeding ratio, high digestibility of the carbon fraction and effective mixing and aeration. The second step is an incubation step (5200) with high C:N ratio, typical carbon content of lower digestibility which at the same time serves as bulking material. The third step is the aging process, which typically proceeds in conventional piles.

The initiation section (5100) consists of a conveying mixer (5101), separated in two parallel compartments (5102) with opposite transport directions driven by individual motors (5104a and b). The first mixer compartment is equipped with a top-loaded feed port (5105), defining the entrance of the initiation section. The initiation/mixer section is fed via a pre-mixing silo (5106) continuously fed with the solid substrate from the three-phase separation unit by means of a screw conveyor (5107a), and via a second screw conveyer (5107b) highly accessible carbon-rich mark-up material may be added such as e.g. glycerol from the biodiesel production, waste from the bakery or fruit industry, or the like. Such mark-up material may also serve to increase the porosity of the substrate or to adjust the properties of the compost being produced. Example of such material is used bleaching earth, potassium from conventional biodiesel production or any other suitable organic waste that is not subjected to the pre-treatment and separation process described here above. The second mixer compartment is equipped with a discharge port at its end (5108). i.e., the exit of the mixer. The discharge port is at the bottom of the far end of the second mixing section. Both compartments are equipped with separately driven shafts providing tilted paddle blades terminated with low clearance (5109).

The paddle blade axes are shown here provided with perpendicular rake blades i.e., parallel to the driving shaft. The two compartments are U-shaped with comparably low clearance of the paddle plates and are parted by a separation plate (5110), except where the far end of the first compartment meets the beginning of the second compartment. At this point the substrate is conveyed from the first to the second compartment by means of shuffling blades at the end of the first compartment. The end section of the second compartment is terminated by shuffling blades and in this section the separation plate is adjustable in height and is typically ½ to ⅔ of the height of the central separation plate. Thus, within the discharge section, which is typically about ⅛ of its total length, a fraction of the substrate is transferred from the second compartment, above the separation plate, back to the first compartment. This fraction serves as seeding material, while the remainder is transferred to the incubation section of the composting unit. The ratio of the material that is transferred for seeding of the fresh substrate and that is transferred to the incubation section may be adjusted by adjusting the height of the separation plate as appropriate. Alternatively, the exit port may be closed and the separation plates may be removed for batch production and extended mixing time. In this configuration the discharge port is opened to empty the mixer between batches. In batch production the mixer is only emptied to an extent providing sufficient seed for the next batch. In either configuration the discharge port of the mixer is connected directly to a screw conveyor (5115) placed below the discharge port (5108).

The screw conveyor (5115) serves to transport the substrate from the initiation section to the incubation section of the composting unit, but at the same time it serves as a mixing unit for the bulking material added before the incubation phase.

This is achieved by a 50% increase in diameter of the screw conveyer on the way from the mixer to the incubation section/container.

A top loaded port for the addition of bulking material (5116) is typically feed via a screw conveyor (5117) through a feed silo (5118), about 0.5-1.0 m downstream from the diameter-increase of the screw conveyor. The screw conveyer connects to a discharge armature (5201), on top of the incubation section (5200), from which discharge may be achieved at distinct points along the incubation section (5202) by removable bottom hatches. The incubation section can be suitably arranged in a 20 or 40 ft transport container with humidification sprayers provided in the top section (5203) and with forced aeration through pressurized air provided in the bottom section (5204).

Where SHW is provided in the process, and separated in to fat and protein components with reduced water content, the protein fraction may be expected to have a C:N ratio of 2-4. Food waste, which constitutes the bulk of the organic fraction of household waste, is typically in the range of 8-10. In this preferred embodiment where the system is presented as whole, the organic fraction to be subjected to compost has passed through the steam explosion and separation unit, thus providing sterilization of potential pathogenic material, and increased digestibility of carbon rich cellulosic material, e.g. paper and diapers, which may constitute an appreciable fraction of HHW. The sterilization through heating in the steam explosion unit may be of special advantage in the case of SHW waste where this is required by regulations, otherwise restricting the use of the compost produced. This is also the case for household waste, especially where such waste contains an appreciable fraction of used diapers as is the case for most urban areas. The so obtained composting material may be balanced with garden waste and, glycerol (e.g. from the biodiesel production), flour, dough, fruit and other carbon rich disposal from the food industry and high sugar content solid disposal from other sources. The C:N ratio in the initiation step may be balanced to achieve a ratio preferably in the range of 15 to 20, but may also be driven in the range from 10 to 15.

Optional Wet-Rendering Unit (6000)

Figure 8:
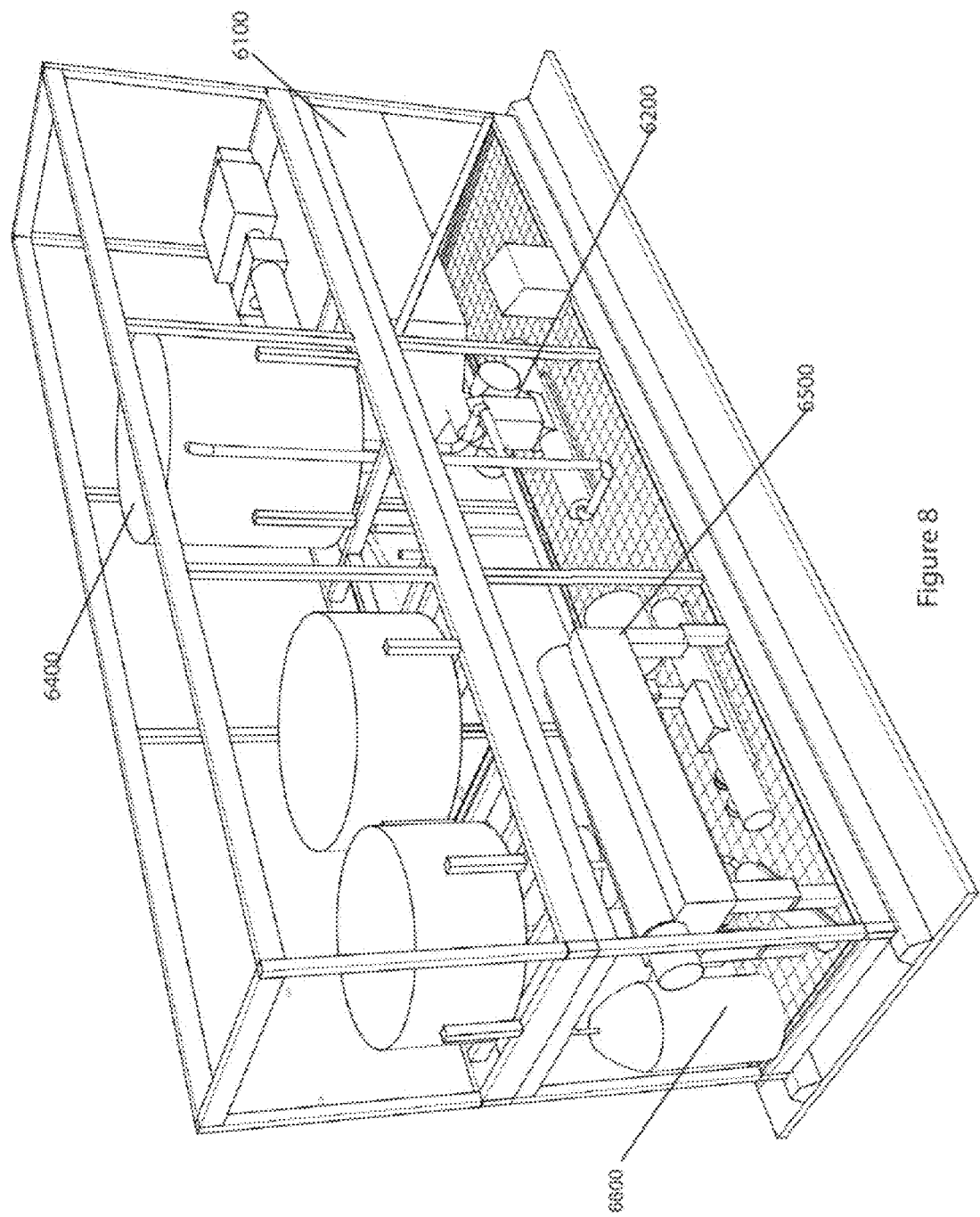
FIG. 8 shows a possible arrangement of a rendering unit according to the invention.

As mentioned above, for waste streams that are rich in fats and/or oils such as slaughterhouse waste (SHW) or waste from the vegetable oil and the fish oil industry (OIW), the system and process may include an optional rendering unit, which is part of the invention. An example of a setup of such unit of the invention is illustrated in FIG. 8, the unit includes in this embodiment a receiving section (6100) from which material is fed through a grinder (6200) and onwards to a heater to raise the temperature of the stream. The heated stream is fed to a melting tank (6400) in which the substrate disintegrates further and proteins coagulate. The substrate is maintained at a temperature in the range of 80-100° C. such as more preferably in a range of about 90-95° C., typically for a period in the range 30-60 minutes, the actual time may depend on the composition of the rendered material. After the heating/melting the substrate is transferred to a decanter (6500) in which an oil/fat phase is separated from aqueous slurry, the aqueous slurry is then further separated by centrifugation in centrifuge (6600) from which is obtained a fraction with solid material, preferably at least 30-40% or more dry matter, this fraction can then be directed to the pre-treatment unit for steam explosion treatment. The aqueous phase from the rendering has preferably sufficiently low solids content such it can be discarded to sewage or water treatment, depending on local requirements.

Energy and Material Balance

The following example provides energy and mass balance calculations for the system as whole, for the purpose to establishing its energy self-sufficiency. The calculations are exemplary, apply to the production of methane and biodiesel and are based on a set of premises detailed herein below. For simplification, neither heat loss nor heat recovery is considered in the thermal energy loop of the system, but the fuel to electricity conversion efficiency is set at 80% including heat recovery in that process. The set of premises may be redefined as reasonably applying to the system, allowing the skilled person to verify the self-sufficiency of the system under different operation conditions:

Material and Composition:

The calculations are based on a material flow rate of 10.000 kg/h or 2.78 kg/sec.

An average incoming waste stream having the following basic composition: water: 60%; fats and/or oils: 15%, dry matter: 25%.

Material Conversion Efficiency:

Fraction of solid converted to methane; 20%

Fraction of fats and/or oils converted to biodiesel 80%

Specific Heat and Heat of Evaporation:

Specific heat of water: 4.2 kJ/kg° C.

Specific heat of the dry matter: 2.1 kJ/kg° C.

Specific heat of fat/oils: 2.0 kJ/kg° C.

Weighted average specific heat: 3.3 kJ/kg° C.

Biodiesel heat of evaporation 360 kJ/kg° C.

Heat of Combustion:

Methane heat of combustion 55.7 MJ/kg

Biodiesel heat of combustion 40 MJ/kg
Main Energy Input:
Thermal;
Material heating from 0° C. to 212° C. for steam explosion; 3,3(kJ/kg° C.)*10.000(kg/h)*212(° C.)=7,000 MJ.
Material reheating from 40° C. to 95° C. after steam explosion but prior to three phase separatin: 3,3(kJ/kg° C.)*10.000(kg/h)*50(° C.)=1.650 MJ
Material heating from 0° C. to 60° C. for conversion of fat/oils to biodiesel; 2.0(kJ/kg° C.)*0.15*10.000(kg/h)*60(° C.)=180 MJ.
Biodiesel heating from 0° C. to 180° C. for distillation; 2.0(kJ/kg° C.)*0.15*10.000(kg/h)*180(° C.)=540 MJ.
Biodiesel heat of evaporation 360 (kJ/kg° C.)*0.15*10.000(kg/h)=570 MJ.
Total thermal energy input without any heat recovery: 7000+1,650+180+540+570=9,940 MJ/h
Electrical;
Electrical input is estimated as 800 MJ/h amounting to about 8% of the thermal energy input. Conversion efficiency is set generically as 80% independent of the fuel used for electricity production assuming efficient heat recovery from the electrical generator for heating water for the steam boiler.
Total electrical energy input with heat recovery 100*800/80=1000 MJ/h
Total energy input into the system=11,000 MJ/h
Fuel Production:
Methane production; 10.000 kg/h*0.25*0.2=500 kg/h
Biodiesel production; 10.000 kg/h*0.15*0.8=1200 kg/h
Heat of Combustion
Total heat of methane combustion; 500 kg/h*55.7 MJ/kg=27,800 MJ/h
Total heat of biodiesel combustion; 1200 kg/h*40 MJ/kg=48,000 MJ/h
Total energy input into the system: 11,000 MJ/h
Total available heat of combustion fuels produced in the system: 75,800 MJ/h
Total net energy balance of the system may be expressed as the difference between the total energy input into the system and the total heat of combustion of fuels produced in the process. In the current example the net energy balance of the system is thus: 75.800 MJ/h–11,000 MJ/h=64.800 MJ/h

The invention claimed is:

1. A waste conversion system, comprising
at least one pre-treatment unit for receiving a stream of waste of which at least a portion thereof being organic waste, the at least one pre-treatment unit comprising at least one continuous-flow steam explosion reactor, wherein said at least one continuous-flow steam explosion reactor is operable as a alkaline steam explosion reactor and comprises a high-pressure retention section and a pressure relief section, and wherein said pressure relief section of the steam explosion reactor serves at the same time as a carbon dioxide scrubbing unit;
at least one separation unit, for receiving a stream of pre-treated waste from said at least one pre-treatment unit, the at least one separation unit comprising at least one conditioning section and at least one separation section for the separation of conditioned waste into at least one fat/oil component, at least one aqueous component material, and solid organic material;
at least one biodiesel production unit, for generating biodiesel from the at least one fat/oil component;
at least one digestion unit, for anaerobic digestion and/or fermentation of the at least one aqueous component; and
at least one composting unit, for the generation of compost from said solid organic material introduced into the composting unit.

2. The system according to claim 1, wherein said high-pressure retention section comprises at least one adjustable-speed conveyor for transporting said stream of waste through said high-pressure retention section.

3. The system according to claim 2, comprising a rotational feed valve at an entrance of the high-pressure retention section for feeding said stream of waste into the high-pressure retention section and comprising a rotational discharge valve for discharging material from said high-pressure retention section.

4. The system according to claim 3, comprising first steam injection means for injecting steam into a loading compartment of said rotational feed valve prior to its rotation to a discharge position and second steam injection means for injecting steam to a discharge compartment of said rotational discharge valve after its discharge into the pressure relief section, prior to its rotation back to its loading position.

5. The system according to claim 3, further comprising a control unit that allows adjustable retention time of material within said high-pressure retention section, by synchronization of the rotational feed valve and the rotational discharge valve and the conveying speed of said at least one adjustable-speed conveyor within the high-pressure retention section.

6. The system according to claim 1, wherein an upper part of the carbon dioxide scrubbing unit is adapted to receive delivery of a stream of material from the high-pressure retention section of the alkaline steam explosion reactor under an angle with respect to the central axis of the carbon dioxide scrubbing unit, to direct said stream of material into a cyclone pattern by means of at least one internal spiral.

7. The system according to claim 6, where the carbon dioxide scrubbing unit comprises two inserted spirals which are vertically offset with respect to each other with an upper spiral of said inserted spirals having clearance from an inner wall of the carbon dioxide scrubbing unit while a lower spiral of said inserted spirals has no clearance from said inner wall, which effectuates a partial velocity component perpendicular to a primary cyclone pattern flow of the stream of waste within the carbon dioxide scrubbing unit, effectuated by material conveyed from the upper spiral to the lower spiral along the inner wall of the carbon dioxide scrubbing unit.

8. The system according to claim 7 wherein said lower spiral is provided with a corrugated pattern partly guiding material towards the center of the carbon dioxide scrubbing unit and a protruding rim at an inner edge of said lower spiral causing a perpendicular component of the material to splash and disperse towards the center of the carbon dioxide scrubbing unit.

9. The system according to claim 1, wherein the carbon dioxide scrubbing unit further comprises at least one carbon dioxide inlet provided within a lower part of the scrubbing unit, whereby an alkaline stream of material from the high-pressure retention section meets a carbon dioxide rich stream to facilitate carbon dioxide scrubbing.

10. The system according to claim 1, wherein said carbon dioxide scrubbing unit is provided with heat exchanging cooling elements providing cooling of said stream of pre-treated waste, which acts as a scrubbing media and which recovers heat from the steam explosion.

11. The system according to claim 1, further comprising means for directing carbon dioxide that is generated within the system into the carbon dioxide scrubbing unit.

12. The system according to claim 1, wherein said at least one pre-treatment unit further comprises a wetting and mixing section upstream of the at least one continuous-flow steam explosion reactor, suitable for wetting and mixing said stream of waste and for adjusting pH of said stream of waste, prior to steam explosion.

13. The system according to claim 1, wherein said at least one digestion unit comprises at least one unit that is configured so that it accommodates methane production or ethanol production depending on the choice of a user and available waste stream material.

14. The system according to claim 1, further comprising a rendering unit upstream of the at least one pre-treatment unit, wherein said rendering unit is configured to separate from said stream of waste at least a portion of a fat/oil component of said stream of waste, and directing said separated portion of fat/oil component to said at least one biodiesel production unit bypassing said at least one pre-treatment unit.

15. The system according to claim 14, wherein a separation section of said rendering unit comprises a centrifugal decanter unit.

16. The system according to claim 14, wherein said at least one digestion unit comprises at least one unit that is configured so that it accommodates methane production or ethanol production depending on the choice of a user and available waste stream material.

17. The system according to claim 1, wherein said at least one composting unit comprises an initiation section and incubation section, said initiation section comprising at least on screw conveyor for transporting said solid organic material from the initiation section to the incubation section.

18. The system according to claim 17, wherein the at least one screw conveyor having an increase in diameter along the conveying direction in the range of about 20-50%, enabling addition of bulking material during the transport of said solid organic material from the initiation section to the incubation section.

19. The system according to claim 18, wherein said at least one pre-treatment unit further comprises a wetting and mixing section upstream of the at least one continuous-flow steam explosion reactor, suitable for wetting and mixing said stream of waste and for adjusting pH of said stream of waste, prior to steam explosion.

20. A process for treating and converting waste, comprising
receiving a stream of waste which comprises at least a portion that is organic waste,
introducing the stream of waste or at least a portion thereof into a wetting and mixing section and wetting and mixing the waste,
transferring the stream of waste from said wetting and mixing section into a continuous-flow steam explosion reactor and subjecting it to steam explosion treatment,
directing the stream of waste treated in said steam explosion reactor to a separation unit, and separating the stream of waste into at least a component comprising fat and/or oil, a component comprising aqueous slurry of organic matter, and a component comprising wet solid organic material,
introducing said component comprising fat and/or oil into a biodiesel production unit, and generating biodiesel from said component comprising fat and/or oil,
introducing said component comprising aqueous slurry into a digestion and/or fermentation unit and digesting and/or fermenting said component comprising aqueous slurry through anaerobic digestion and/or fermentation, and
introducing said component comprising wet solid organic material into a composting unit,
wherein said step of separating in the separation unit comprises feeding said stream of waste treated in said steam explosion reactor into a separation tank of an oil or fat separation section, delivering microbubbles to said separation tank, removing fat or oil that accumulates on a liquid surface within said separation tank, and feeding said component comprising aqueous slurry from said separation tank to a liquid-solid separator, feeding from said liquid-solid separator said component comprising wet solid organic material to said composting unit, and said feeding component comprising aqueous slurry of organic matter to said anaerobic unit of fermentation unit.

21. The process according to claim 20, wherein said step of introducing said component comprising wet solid organic material into said composting unit comprises feeding said component at a temperature in the range of about 40-50° C. to an initiation section of said composting unit to accelerate the process by subjecting said component directly to thermophile digestion and bypassing mesophilic stage composting, further comprising transferring said wet solid organic material from said initiation section to a second stage incubation section of said composting unit with addition of bulking material, aerating said wet solid organic material in said incubation section with forced aeration and humidifying said wet solid organic material, and incubating said wet solid organic material in said incubation section for a period of time in the range of about 24-96 hours.

22. The process according to claim 21, wherein said steam explosion treatment is conducted at a pressure in the range of about 10 to 40 bars and at a temperature in the range of about 180 to about 250° C.

23. The process according to claim 21, wherein said separation unit comprises a conditioning section, wherein prior to said separating, said stream of waste treated in said steam explosion reactor is conditioned in said conditioning section by introducing acid solution and/or other solution and by mixing.

24. The process according to claim 20, wherein the process is energy self-sufficient, such that the process does not require external sources of energy.

25. The process according to claim 20, wherein said steam explosion treatment is conducted at a pressure in the range of about 10 to 40 bars and at a temperature in the range of about 180 to about 250° C.

26. The process according to claim 20, wherein said separation unit comprises a conditioning section, wherein prior to said separating, said stream of waste treated in said steam explosion reactor is conditioned in said conditioning section by introducing acid solution and/or other solution and by mixing.

27. A waste conversion system, comprising
at least one pre-treatment unit for receiving a stream of waste of which at least a portion thereof being organic waste, said at least one pre-treatment unit comprising a continuous-flow steam explosion reactor;
at least one separation unit, for receiving a stream of pre-treated waste from said at least one pre-treatment unit, the at least one separation unit comprising at least one conditioning section and at least one separation section for the separation of conditioned waste into at least one fat/oil component, at least one aqueous component, and solid organic material;

at least one biodiesel production unit, for generating biodiesel from the at least one fat/oil component;

at least one digestion unit, for anaerobic digestion and/or fermentation of the at least one aqueous component; and at least one composting unit, for the generation of compost from said solid organic material, wherein said continuous-flow steam explosion reactor comprises a high-pressure retention section and a pressure relief section and wherein said high-pressure retention section comprises at least one adjustable-speed conveyor for transporting said stream of waste through said high-pressure retention section, and wherein said continuous-flow steam explosion reactor comprises a rotational feed valve at an entrance of the high-pressure retention section for feeding said stream of waste into the section and comprising a rotational discharge valve for discharging material from said high-pressure retention section.

28. The system according to claim 27, comprising first steam injection means for injecting steam into a loading compartment of said rotational feed valve prior to its rotation to a discharge position and second steam injection means for injecting steam to a discharge compartment of said rotational discharge valve after it's discharge into the pressure relief section, prior to its rotation back to its loading position.

29. The system according to claim 27, further comprising a control unit that allows adjustable retention time of material within said high-pressure retention section, by synchronization of the rotational feed valve and the rotational discharge valve and the conveying speed of said at least one adjustable-speed conveyor within the high-pressure retention section.

30. The system according to claim 27, wherein said at least one pre-treatment unit further comprises a wetting and mixing section upstream of the continuous-flow steam explosion reactor, suitable for wetting and mixing said stream of waste and for adjusting pH of said stream of waste, prior to steam explosion.

31. A waste conversion system, comprising at least one pre-treatment unit for receiving a stream of waste of which at least a portion thereof being organic waste, said at least one pre-treatment unit comprising a continuous-flow steam explosion reactor;

at least one separation unit, for receiving a stream of pre-treated waste from said at least one pre-treatment unit, the at least one separation unit comprising at least one conditioning section and at least one separation section for the separation of conditioned waste into at least one fat/oil component, at least one aqueous component, and solid organic material;

at least one biodiesel production unit, for generating biodiesel from the at least one fat/oil component;

at least one digestion unit, for anaerobic digestion and/or fermentation of the at least one aqueous component; and at least one composting unit, for the generation of compost from said solid organic material, wherein said at least one biodiesel production unit comprises a continuous-flow biodiesel reactor, adapted to receive a continuous flow of said at least one fat/oil component and thereby generate a continuous flow of biodiesel, wherein said continuous-flow biodiesel reactor comprises a plurality of contact plates coated on one side with esterification and/or transesterification catalyst, whereby alternating two coated sides face each other and two non-coated sides face each other and said at least one fat/oil component flows between the coated sides of the contact plates while a thermal media for temperature control of reactants flows between the non-coated sides of the contact plates.

32. A waste conversion system, comprising at least one pre-treatment unit for receiving a stream of waste of which at least a portion thereof being organic waste, said at least one pretreatment unit comprising a continuous-flow steam explosion reactor;

at least one separation unit, for receiving a stream of pre-treated waste from said at least one pre-treatment unit, the at least one separation unit comprising at least one conditioning section and at least one separation section for the separation of conditioned waste into at least one fat/oil component, at least one aqueous component, and solid organic material;

at least one biodiesel production unit, for generating biodiesel from the at least one fat/oil component;

at least one digestion unit, for anaerobic digestion and/or fermentation of the at least one aqueous component; and at least one composting unit, for the generation of compost from said solid organic material, wherein said at least one composting unit comprises an initiation section and an incubation section, said initiation section comprising at least one screw conveyor for transporting substrate from the initiation section to the incubation section, the at least one screw conveyor having an increase in diameter along the conveying direction in the range of about 20-50%, enabling addition of bulking material during the transport of said solid organic material from the initiation section to the incubation section.

33. The system according to claim 32, wherein said at least one digestion unit comprises at least one unit that is configured so that it accommodates methane production or ethanol production depending on the choice of a user and available waste stream material.

34. The system according to claim 32, wherein said incubation section comprises humidification sprayers and means for forced aeration.

35. A waste conversion system, comprising at least one pre-treatment unit for receiving a stream of waste of which at least a portion thereof being organic waste, said at least one pretreatment unit comprising a continuous-flow steam explosion reactor;

at least one separation unit, for receiving a stream of pre-treated waste from said at least one pre-treatment unit, the separation unit comprising at least one conditioning section and at least one separation section for the separation of conditioned waste into at least one fat/oil component, at least one aqueous component, and solid organic material;

at least one biodiesel production unit, for generating biodiesel from the at least one fat/oil component;

at least one digestion unit, for anaerobic digestion and/or fermentation of the at least one aqueous component; and at least one composting unit, for the generation of compost from said solid organic material, the system further comprising a rendering unit upstream of the at least one pre-treatment unit, wherein said rendering unit is configured to separate from said stream of waste at least a portion of a fat/oil component of said stream of waste, and directing said portion of fat/oil component to said at least one biodiesel production unit bypassing said at least one pre-treatment unit.

36. A process for treating and converting waste, comprising
receiving a stream of waste which comprises at least a portion that is organic waste,
introducing the stream of waste or at least a portion thereof into a wetting and mixing section and wetting and mixing the waste,
transferring the stream from said wetting and mixing section into a continuous-flow steam explosion reactor and subjecting it to steam explosion treatment,
directing a stream of waste treated in said steam explosion reactor to a separation unit, and separating the pre-treated waste stream into at least a component comprising fat and/or oil, a component comprising aqueous slurry of organic matter, and a component comprising wet solid organic material,
introducing said fat and/or oil component into a biodiesel production unit, and generating biodiesel from said fat/oil component,
introducing said component comprising aqueous slurry into a digestion and/or fermentation unit and digesting and/or fermenting said component through anaerobic digestion and/or fermentation,
introducing said component comprising wet solid organic material into a composting unit, wherein said step of introducing said component comprising wet solid organic material into said composting unit comprises feeding said component at a temperature in the range of about 40-50° C. to an initiation section of said composting unit to accelerate the process by subjecting the substrate directly to thermophile digestion and bypassing mesophilic stage composting, further comprising transferring said wet solid organic material from said initiation section to a second stage incubation section of said composting unit with addition of bulking material such as wood chips, aerating said wet solid organic material in said incubation section with forced aeration and humidifying said wet solid organic material, and incubating the material in said incubation section for a period of time in the range of about 24-96 hours.

* * * * *